United States Patent
Finkelstein et al.

(10) Patent No.: US 11,125,753 B2
(45) Date of Patent: Sep. 21, 2021

(54) LABELING USING AN OPTICAL THICKNESS MEASUREMENT OF A BIOSENSOR

(71) Applicant: TruTag Technologies, Inc., Kapolei, HI (US)

(72) Inventors: Hod Finkelstein, Berkeley, CA (US); Timothy Learmonth, Berkeley, CA (US)

(73) Assignee: TruTag Technologies, Inc., Kapolei, HI (US)

( * ) Notice: Subject to any disclaimer, the term of this patent is extended or adjusted under 35 U.S.C. 154(b) by 431 days.

(21) Appl. No.: 15/934,538

(22) Filed: Mar. 23, 2018

(65) Prior Publication Data
US 2018/0284121 A1    Oct. 4, 2018

Related U.S. Application Data

(60) Provisional application No. 62/478,238, filed on Mar. 29, 2017.

(51) Int. Cl.
| | |
|---|---|
| *G01J 3/00* | (2006.01) |
| *G01N 21/45* | (2006.01) |
| *G01J 3/45* | (2006.01) |
| *G01N 21/63* | (2006.01) |
| *G01N 33/58* | (2006.01) |

(Continued)

(52) U.S. Cl.
CPC ........... *G01N 33/58* (2013.01); *C12Q 1/6816* (2013.01); *C12Q 1/6876* (2013.01); *G01J 3/00* (2013.01); *G01J 3/26* (2013.01); *G01J 3/45* (2013.01); *G01N 21/45* (2013.01); *G01N 21/63* (2013.01); *G01N 21/77* (2013.01); *G01N 21/8483* (2013.01); *G01N 21/31* (2013.01); *G01N 2021/458* (2013.01);
(Continued)

(58) Field of Classification Search
None
See application file for complete search history.

(56) References Cited

U.S. PATENT DOCUMENTS

| | | | |
|---|---|---|---|
| 6,248,539 B1 * | 6/2001 | Ghadiri | G01N 21/45 385/12 |
| 7,517,656 B2 * | 4/2009 | Martin | B01L 3/5023 385/12 |

(Continued)

FOREIGN PATENT DOCUMENTS

WO    WO-2017132270 A1    8/2017

*Primary Examiner* — Neil N Turk
(74) *Attorney, Agent, or Firm* — Van Pelt, Yi & James LLP

(57) ABSTRACT

A system detects an analyte suspected of being present in a sample. The reader reads an optical tag on a substrate, which is configured to immobilize the tag on a substrate surface. The optical tag is bound to a probe and includes a plurality of pores that create an effective index of refraction. The plurality of pores and a thickness of the tag are selected for a reflectance property. The substrate is configured to contact a sample suspected of comprising an analyte. The probe is capable of binding specifically to the analyte. The reader is configured to expose the tag to light to generate a sample spectral signature that is a function of the effective index of refraction, the thickness of the optical tag, and whether the analyte is coupled to the probe. The sample spectral signature is compared to a reference to detect the analyte in the sample.

43 Claims, 10 Drawing Sheets

(51) Int. Cl.
  *C12Q 1/6876* (2018.01)
  *G01N 21/77* (2006.01)
  *C12Q 1/6816* (2018.01)
  *G01N 21/84* (2006.01)
  *G01J 3/26* (2006.01)
  *G01N 21/31* (2006.01)

(52) U.S. Cl.
  CPC ............... *G01N 2021/7773* (2013.01); *G01N 2021/7776* (2013.01); *G01N 2021/7779* (2013.01)

(56) References Cited

U.S. PATENT DOCUMENTS

| | | | |
|---|---|---|---|
| 9,290,816 B2* | 3/2016 | Pregibon | C12Q 1/6825 |
| 2003/0146109 A1 | 8/2003 | Sailor | |
| 2007/0019198 A1* | 1/2007 | Tuschel | G01J 3/02 |
| | | | 356/432 |
| 2007/0252983 A1 | 11/2007 | Tong | |
| 2008/0272312 A1* | 11/2008 | Tuschel | G01N 21/6452 |
| | | | 250/459.1 |
| 2010/0227414 A1 | 9/2010 | Ervin | |
| 2014/0034497 A1* | 2/2014 | Davis | G01N 27/44791 |
| | | | 204/451 |
| 2014/0147883 A1 | 5/2014 | Prins | |
| 2015/0361418 A1 | 12/2015 | Reed | |
| 2016/0066775 A1* | 3/2016 | Hunter | G01J 3/45 |
| | | | 600/178 |
| 2016/0123809 A1* | 5/2016 | Learmonth | G01N 21/255 |
| | | | 356/454 |

\* cited by examiner

LABELING USING AN OPTICAL THICKNESS MEASUREMENT OF A BIOSENSOR

CROSS REFERENCE TO OTHER APPLICATIONS

This application claims priority to U.S. Provisional Patent Application No. 62/478,238 entitled LABELING USING AN OPTICAL THICKNESS MEASUREMENT OF A BIOSENSOR filed Mar. 29, 2017 which is incorporated herein by reference for all purposes.

BACKGROUND OF THE INVENTION

Molecular labels have been used to determine the identity and presence of an analyte as it reacts with a probe. The use of labels in a detection process however, can affect the properties of the analyte and lead to undesirable and unanticipated interactions. Although label-free detection has been achieved, it requires expensive components, is time consuming, and has not been demonstrated for multiplexed detection for large numbers of analytes. For example, traditional labels such fluorophores are costly, their attachment to an analyte is time-consuming, and they require sophisticated and expensive instruments for detection. Some label free methods of detection use a shift in resonance energy of plasmonic waves to detect an incorporation on a substrate. Such methods require a coherent light source, very fine optical alignment in order to induce the plasmonic wave, and expensive substrates, typically gold. Furthermore, in order to multiplex targets, multiple substrates need to be created, each with its own optically-aligned light source. Another example of a label-free method uses a shift in the resonant wavelength of a ring resonator upon successful incorporation of a target onto the surface of the ring resonator. This method requires expensive optics with a coherent source in order to couple into an array of waveguides (or a very lossy incoherent source), expensive lithography to create the resonators, and very fine spectroscopes to measure fine shifts in wavelength. Moreover, the available surface area of the ring resonator limits the sensitivity of such devices. These label-free detection techniques are limited with respect to the number of targets that can be simultaneously detected on an array of resonators. As a result, there is an unmet need in the art for a highly multiplexed, label-free method to identify a set of target analytes in a sample quickly, robustly, and inexpensively.

BRIEF DESCRIPTION OF THE DRAWINGS

Various embodiments of the invention are disclosed in the following detailed description and the accompanying drawings.

DETAILED DESCRIPTION

Figure 1:
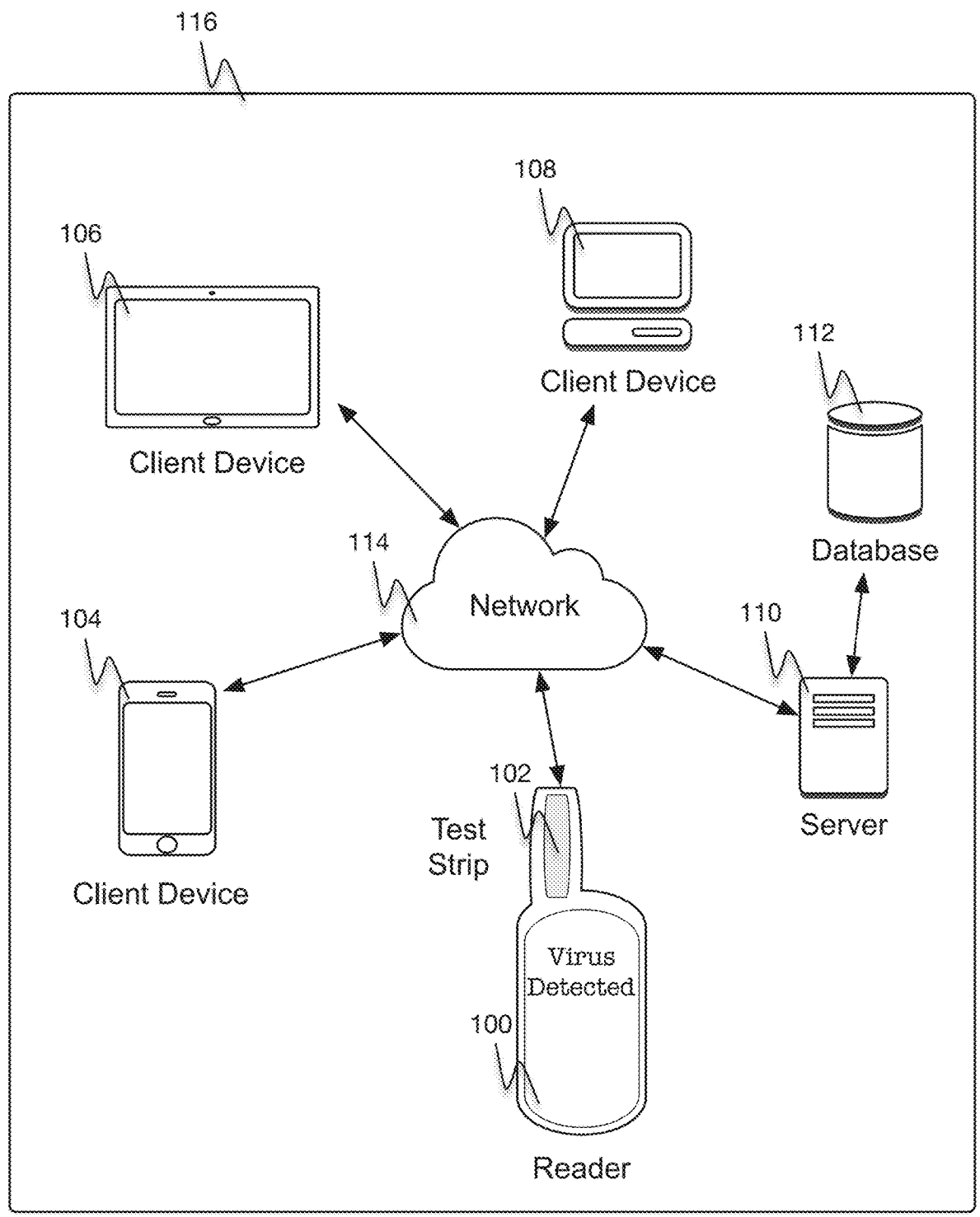
FIG. 1 is a diagram illustrating an embodiment of a system for labeling using an optical thickness measurement of a biosensor.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A system for labeling using an optical thickness measurement of a biosensor is disclosed. The system is configured to detect an analyte suspected of being present in a sample and comprises a reader where the reader reads an optical tag on a substrate. The substrate is configured to immobilize an optical tag on a surface of the substrate. The optical tag is bound to a probe and comprises a plurality of pores that creates an effective index of refraction. The plurality of pores and a thickness of the optical tag are selected for a reflectance property of the optical tag where the reflectance property and probe are associated with each other. The substrate is further configured to place in contact a sample suspected of comprising an analyte where the probe is capable of binding specifically to the analyte.

The reader is configured to expose the optical tag to electromagnetic radiation to generate a sample spectral signature that is a function of the effective index of refraction, the thickness of the optical tag, and whether the analyte is coupled to the probe. The sample spectral signature is compared to a reference spectral signature to detect the analyte in the sample.

By observing a shift in a spectral signature generated upon illumination of the optical tag, the system implements a label-free method of detecting a target molecule's reaction with functionalized optical tags. A "shift" in a spectral signature refers to any observed change in the spectral signature. For example, comparing the sample spectral signature with the reference spectral signature comprises identifying the presence or absence of a spectral signature shift between the sample spectral signature and the reference spectral signature. In some embodiments, detection of the spectral signature shift indicates the presence of the analyte in the sample. For example, the spectral signature shift comprises a shift in a peak placement or peak number. In some embodiments, the reference spectral signature is acquired by exposing the optical tag to electromagnetic radiation prior to having the sample come in contact with the substrate and stored in a memory. In some embodiments, the reference spectral signature is determined from a functionalized or non-functionalized optical tag before contact with the sample or is directly measured or statistically determined. In some embodiments, the detection of the sample spectral signature comprises detecting an intensity at 20 or more, 30 or more, 40 or more, 50 or more, 60 or more, 70 or more, 80 or more, 90 or more, or 100 or more different narrow wavelength bands from a single one of the optical tags on the substrate. In some embodiments, the sample spectral signature comprises obtaining a wide spectral range from a field of view of about 100 mm$^2$.

In various embodiments, the sample is liquid, air, or vapor, or part of a liquid assay or Non-Invasive Prenatal Test (NIPT) test. For example, placing in contact the plurality of optical tags with the sample comprises mixing the optical tag with the sample in a solution or in a gaseous environment. In some embodiments, the optical tag is separated from the fluid sample using centrifugation, filtration, or electrophoresis.

In some embodiments, the sample spectral signature comprises a Fabry-Perot spectral response. In some embodiments, detection of the sample spectral signature comprises placing the substrate in the reader which is capable of obtaining the spectral signature. For example, the reader displays an identity of the analyte upon detection. In some embodiments, the reader comprises an interferometer. For example, the interferometer is a tunable Fabry-Perot interferometer or a Michelson type interferometer.

In various embodiments, the optical tag comprises silica or silicon, is partially oxidized or fully oxidized, comprises a non-silica dielectric, or has a porosity of 60 to 95%. In some embodiments, the optical tag comprises a silica linker. For example, the silica linker is an organofunctional alkoxysilane molecule. In some embodiments, the plurality of pores of the optical tag is sufficiently large to facilitate entry of the analyte into the plurality of pores while excluding non-target molecules. In some embodiments, the plurality of unique optical tags is configured to generate a unique spectral signature comprising at least one peak that is a function of the effective index of refraction of a unique optical tag and the thickness of the unique optical tag. For example, the identity of the probe is correlated with the unique optical tag. In some embodiments, optical tag has a diameter, length, width, depth or height that is less than or equal to a millimeter. In some embodiments, the optical tag is immobilized prior to or after the sample comes in contact with the optical tag.

In various embodiments, the probe is bound within one of the plurality of pores of the optical tag. For example, the probe comprises an oligonucleotide or a polypeptide, a receptor, an aptamer, an antibody or an antibody fragment, or a layer of amino acids across the surface of the optical tag. In some embodiments, the probe is label free. In various embodiments, a label comprises a marker, a florescent marker, a chemical marker, a physical bead, or any other appropriate label.

In various embodiments, the substrate comprises glass, paper, plastic, a polymer, or any combination thereof. For example, the substrate comprises a plurality of unique optical tags immobilized on the surface of the substrate. In some embodiments, the substrate comprises a plurality of the optical tags, wherein the concentration is determined from a proportion of the plurality of optical tags generating a shifted spectral signature or is determined from a change in an average spectral signature for the plurality of optical tags. In some embodiments, the substrate is washed to remove non-specifically bound molecules. For example, the substrate is washed with buffer or air. In some embodiments, the sample is exposed to an electric field during contact with the substrate. In some embodiments, the substrate comprises a filter with pores that are smaller than the size the optical tag.

In various embodiments, detecting the analyte in the sample comprises determining a presence of, an absence of, or a property of the analyte in the sample. For example, the property of the analyte is a concentration, a binding affinity to the probe, or a specific activity of the analyte. In some embodiments, the analyte undergoes a nucleic acid amplification reaction before contacting the substrate with the sample, wherein the analyte is a polynucleotide. For example, the nucleic acid amplification reaction is a polymerase chain reaction, an isothermal amplification reaction, or a recombinase polymerase amplification reaction. In some embodiments, the analyte is purified from the sample using magnetic beads or is label free.

In porous silica biosensing, a change in the effective optical thickness of a functionalized silica film in response to the introduction of a target molecule signals the presence of the target molecule. The effective optical thickness of a homogeneous film is the product of the thickness of the film and the refractive index of the film and can be readily measured by taking the Fourier transform of a white light reflectance measurement. To measure the optical thickness, the strongest peaks of the Fourier transform of a broadband reflectance measurement can be used. There is a peak for each layer in the film, with an amplitude that depends on the magnitude of the discontinuity in index at the layer boundaries. Since the change in effective optical thickness is what's measured, the absolute effective optical thickness is thus a free variable that can be controlled during biosensor manufacturing and measured during the biosensing experiment.

For example, if the biosensing film is nominally 5 um thick, two layer films can be created that have the 5 um thick biosensing layer, and an additional ID layer that is 4, 5, 6, or 7 um thick. In this example, the ID layer would have the same porosity in each case. The ID layer in these films would have a refractive index of n, since the porosity in each of the ID layers would be the same. The optical thickness of each ID layer would thus be 4 n, 5 n, 6 n, and 7 n um. These films can be removed from the Si wafer, broken into pieces of a desired size distribution, partially or fully oxidized if desired, and functionalized such that each ID layer optical thickness corresponds to a different probe molecule. As a result, the film pieces with a 4 n optical thickness ID layer would be functionalized with probe A, the film pieces with a 5 n optical thickness would be functionalized with probe B, etc. A mixture of the film pieces can be immobilized with the biosensing layer exposed in a flow cell and exposed to an unknown target. By measuring a sufficient sample of the film pieces via optical reflectance, a signal can be recovered that shows the presence or absence of a target, by measuring the change in optical thickness of the biosensing layer, and the effective optical thickness of the ID layer. Each film piece can be identified by the optical thickness of the ID layer, measured by taking the Fourier transform of the optical reflectance spectrum. The probe molecule to which a target attaches can be identified from the mix of probe molecules present in the flow cell. Alternatively, the film pieces can be identified by measuring the total optical thickness of the ID layer and the biosensing layer.

In some embodiments, the biosensing layer itself can also be the ID layer, with its real-space thickness used for ID purposes and its porosity optimized for efficient biosensing. In some embodiments, two sensing layers are used with a variable optical thickness layer in between, such that either side of the film piece could be exposed to the target.

In some embodiments, additional layer(s) can be added to increase the mechanical stability of the film or film piece, working either as a purely mechanical layer or both a mechanical and labelling layer.

In some embodiments, the methods described above can be used without the biosensing layer, and function as a unique identifier that could be attached via glue, coating, lamination, or other method to an object to be later tracked or identified. The uniqueness of the film pieces produced in this way is generated by controlling the optical thickness of the film, in a similar method as described above, and the film piece optical thickness can be linked to a database containing information about the object to which the film piece was attached.

In some embodiments, the method of controlling the optical thickness of a film piece or an ID layer can be used in conjunction with existing methods of producing porous silica or silicon film pieces with information present in the optical reflectance spectrum, for example to increase the number of uniquely identifiable film pieces that can be produced.

FIG. 1 is a diagram illustrating an embodiment of a system for labeling using an optical thickness measurement of a biosensor. In the example shown, the system environment 116 further includes one or more client devices (e.g., client device 104, client device 106, client device 108, etc.), server 110, a database 112 accessible to the server 110, where all of these parties are connected through a network 114. In other embodiments, different and/or additional entities can be included in the system environment 116.

Test strip 102 is prepared with one or more tags that include probes for different analytes. In general, a single thickness tag has probes for a single type of analyte. Test strip 102 is exposed to a sample possibly containing an analyte. Test strip 102 is then further prepared (e.g., washed, dried, etc.) and test strip 102 is placed in reader 100 for detecting the presence or absence of the analyte. In some embodiments, a base spectrum is stored within reader 100 to compare a sample spectrum to. In the event that the spectra are the same, no analyte is detected. In the event that the spectra are different, an analyte is detected. In some embodiments, the base spectrum is retrieved from database 112 for comparison.

The system environment 116 allows the results from the reader 100 to be shared via network 114 with one or more other users at their client devices, including being shared with family, friends, physicians or other medical personnel, schools, civil response teams, among others. Results can also be uploaded to the web.

The network 114 facilitates communications between the components of the system environment 116. The network 114 may be any wired or wireless local area network (LAN) and/or wide area network (WAN), such as an intranet, an extranet, or the Internet. In various embodiments, the network 114 uses standard communication technologies and/or protocols. Examples of technologies used by the network 114 include Ethernet, 802.11, 3G, 4G, 802.16, or any other suitable communication technology. The network 114 may use wireless, wired, or a combination of wireless and wired communication technologies. Examples of networking protocols used for communicating via the network 114 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 114 may be represented using any suitable format, such as hypertext markup language (HTML) or extensible markup language (XML). In some embodiments, all or some of the communication links of the network 114 may be encrypted using any suitable technique or techniques.

The client device(s) is/are computing devices capable of receiving user input as well as transmitting and/or receiving data via the network 114. In some embodiments, client device 104 is a conventional computer system, such as a desktop or laptop computer. Alternatively, client device 104 may be a device having computer functionality, such as a personal digital assistant (PDA), a mobile telephone, a smartphone or another suitable device. A client device 104 is configured to communicate via the network 114.

In some embodiments, the system environment 116 may include one or more servers, for example where the diagnostic system includes a service that is managed by an entity that communicates via the network 114 with reader 100 and/or any of the client devices. Server 110 can store data in database 112 and can access stored data in database 112. Database 112 may be an external database storing medical information, user or patient history data, etc. Server 110 may also store data in the cloud. In some embodiments, server 110 may occasionally push updates to reader 100, or may receive result data from reader 100 and perform certain analyses on that result data and provide the analyzed data back to reader 100 or to a client device.

In some embodiments, reader 100 functionality can be included in a client device, such as a mobile phone, and can be operated via a mobile application installed on the phone. In these cases, a device may be attached to the phone that allows the phone to read the test strip, or the phone's own internal hardware (e.g., imaging hardware) can be used to read the test strip. The mobile application stored on the phone can process the results read from the test strip and share the results with other devices on network 114.

Figure 2:
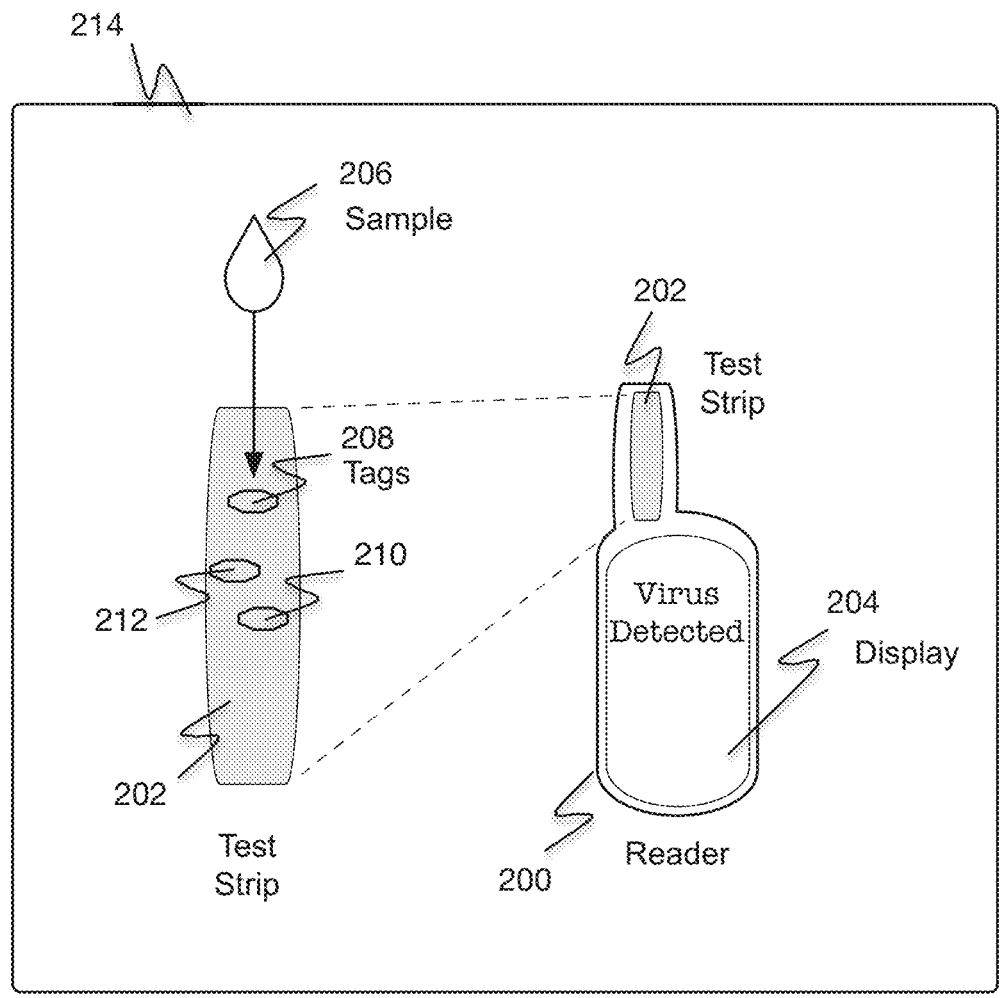
FIG. 2 is a block diagram illustrating an embodiment of a reader.

FIG. 2 is a block diagram illustrating an embodiment of a reader. In some embodiments, reader 200 is used to implement reader 100 of FIG. 1. In some embodiments, the functionalized optical tags (e.g., tags 208, tags 210, and tags 212) are included as part of a system, such as a diagnostic system or platform that provides highly-multiplexed consumer diagnostic results to users. Such a system can be used to detect various different analytes, including pathogens and biomarkers. It can be a low-cost system designed such that a single test can replace a large number of different discreet laboratory tests.

Test strip 202 in this example can be prepared using a library of functionalized optical tags (e.g., porous silicon) deposited on plastic, paper, glass, or another material. In some embodiments, the optical tag functionalization occurs in large batches (e.g., hundreds of millions of tags at a time). Various methods can also be used in applying the optical tags to the test strip, including any of the methods described previously. In some embodiments, a powder is formed of batch functionalized tags with a specific coating and a target. This process is repeated for other target batches, each with its own tag signature but similar reference energy. In some embodiments, equal or known quantities of tags from all batches are mixed. The substrate strips (e.g., test strip 202) can be coated with an adhesive surface or other material with adhesive properties and then sprayed with the tag powder. Test strip 202 can then be packaged and provided to users for use in the diagnostic platform.

Users can apply sample 206 to test strip 202 in various manners, such as by licking the strip, spitting onto the strip, pipetting sample onto the strip, delivering sample via capillary action, amongst other options. In this example, the sample may be a body fluid, such as saliva or blood. In some embodiments, there is a wash step following the application of the sample to the strip. In some embodiments, various other sample preparation steps occur, such as a cell lysis step.

Substrates of the disclosure may comprise any material that can withstand the methods of the disclosure, including any solvents used, without degradation. Exemplary substrates of the disclosure include, but are not limited to, glass, paper, plastic, a polymer, or any combination thereof. As one example, the substrate can be a test strip (e.g., as test strip 202) or other device for receiving a sample. Substrates of the disclosure may further comprise a coating material suitable for immobilizing the plurality of optical tags. Exemplary coating materials include, but are not limited to, a glue, an adhesive, a resin, or a molecule with affinity to the optical tag material to which optical tags of the disclosure attach. Optionally, the substrate comprising a coating material, such as a resin and in contact with a plurality of optical tags, may be cured to immobilize the optical tags within the resin or the substrate.

Substrates may comprise one or more fluidic channels forming at least one inlet and at least one outlet. In some embodiments, at least one surface of the one or more fluidic channels is optically visible/detectable in the spectral band of illumination and imaging. In some embodiments, one or more fluidic channels leads to a chamber or other device that provides a mechanism to detect the spectral band of illumination and imaging of the optical tags.

Substrates can include fluidic actuation elements such as electrodes (in the context of a digital fluidics system), membranes (in the case of pressure-induced fluidics actuation), etc. In some embodiments, substrates comprise electrodes operably connected to assist in increasing the concentration of target molecules at the porous surface and/or to assist in removing non-specifically bound material from the pores upon completion of target incubation in the pores.

Substrates that comprise a coating material can contact the coating material by submersion of the substrate in the coating material or infusion of the substrate with the coating material. In some embodiments, the substrate is porous and, furthermore, may contain one or more fluidic channels.

In some embodiments, substrates comprise one or more topographic features that physically capture a plurality of optical tags upon contact. For example, one or more topographic features of the substrate may include an arrangement of concave or convex impressions and/or protrusions that may be oriented randomly or in a pattern. For example, the substrate may include an arrangement of concave or convex impressions and/or protrusions (e.g., pits or grooves) that are printed, embedded or etched onto the substrate. The substrate may include a lithographically-defined or otherwise fabricated to comprise an arrangement of adhesive features that may be concave or convex impressions and/or protrusions. The substrate may include fibers which are used to non-specifically capture silica optical tags.

In some embodiments, the optical tags are dried and deposited on a substrate such that they are immobilized on the substrate at a preferential orientation. In some embodiments, the optical tags are immobilized such that parallel faces of a silica optical tag are largely parallel to the surface of the substrate. In some embodiments, optical tags immobilized to the surface of the substrate are oriented randomly with respect to the surface of the substrate.

In some embodiments, deposition of the optical tags on the surface of a substrate may be achieved by spray. In some embodiments, optical tags may be embedded in a solvent and then sprayed on a substrate, and the solvent may be wholly or partially disintegrated, for example by evaporation, such that the top surfaces of the optical tags are exposed. In some embodiments, the optical tags may be flowed over a substrate, either via a nozzle or through a fluidic channel and allowed to settle or bond to the substrate, such that the top surfaces of the optical tags are exposed.

In some embodiments, the substrate comprises a sticky substance, such as a glue or resin, which facilitates immobilization of the optical tags to the substrate. In some embodiments, the substance is subsequently cured to affix the tags to the substrate. In some embodiments, electromagnetic radiation may be used to immobilize the optical tags on the substrate—for example, by initiating cross-linking of an adhesive.

In some embodiments, optical tags are immobilized to the surface of a substrate by laminating the substrate comprising optical tags on the surface with a porous material comprising pores smaller than the size of a significant percentage of the tags but larger than the size of the target molecules.

In some embodiments, a mechanical force is applied to align the surfaces of the optical tags parallel to the surface of the substrate. In some embodiments, the mechanical force is provided by a comb, a laminate, a roller or a sufficiently flat object pulled parallel to the surface of the substrate. In some embodiments, the optical tags may be physically captured on a substrate—for example, between fibers or within topographical features present or formed on the substrate. In some embodiments, the coating or adhesive used to bind the particles to the substrate provide an attractive force normal to the substrate surface to orient the flat surface of the optical tags in a configuration that is parallel to the surface of the substrate.

Compositions and/or coating materials of the disclosure may be heated or cooled relative to ambient or room temperature to facilitate contact, immobilization, or orientation of the plurality of optical tags to a surface of the substrate.

In some embodiments, multiple unique optical tags each encoded to generate a unique spectral signature (i.e., a known optical spectral code associated with one or more specific attributes of a reflectance or transmission spectrum)

are applied to a substrate. Each unique spectral signature is associated with at least one probe and target entity. In some embodiments, the number of tags of each type is inversely proportional to the relative sensitivity of the probe in that tag to its target. In other words, the higher the affinity of a certain probe to its target, the fewer tags containing that probe will be incorporated onto a substrate. And similarly, the higher the required sensitivity of a certain probe to its target, for example, because the target is expected to be found in lower concentrations, or has a lower binding affinity, the more tags containing that probe will be incorporated on the substrate or test strip.

Reader 200 is used to read test strip 202. For example, test strip 202 is inserted into reader 200, placed on or inside the reader, scanned by the reader on a surface, or otherwise read by reader 200. In some embodiments, reader 200 is a diagnostic device or instrument. In some embodiments, reader 200 is a compact hyperspectral imaging device that simultaneously images and decodes multiple tags (e.g., hundreds or thousands of tags) in a large field of view. Reader 200 identifies tags whose spectrum has shifted due to a binding event. In other words, binding events of label-free analytes can be optically detected as spectral shifts of tag reflectance peaks or troughs. Reader 200 then reads the optical spectral code associated with the tags, and determines the identity of the analyte. For example, the system can detect a pathogen, such as an influenza pathogen. In some embodiments, reader 200 includes display 204, such as a screen, that allows it to display to the user the results of the test. In some embodiments, the confidence level of the detection can also be determined and provided for display on display 204 of reader 200.

In some embodiments, a software program installed on reader 200 may compare one or more spectral signature(s) from optical tags in a reference image. The program may then identify those optical tags that demonstrate a spectral shift greater than a pre-determined threshold. The threshold may be set to distinguish one or more spectral shifts from standard measurement noise and/or one or more spectral shifts resulting from a non-specific molecular interaction. The program then decodes the optical spectral code in the shifted spectra optical tags. In some embodiments, the software program is a computer readable medium storing instructions on reader 200 that when executed by a processor within reader 200 cause the processor to perform certain actions, such as reading the test strip or storing certain data. In some embodiments, the software program comprises one or more software modules that perform each of the various functions described above for the reader.

Figure 3:
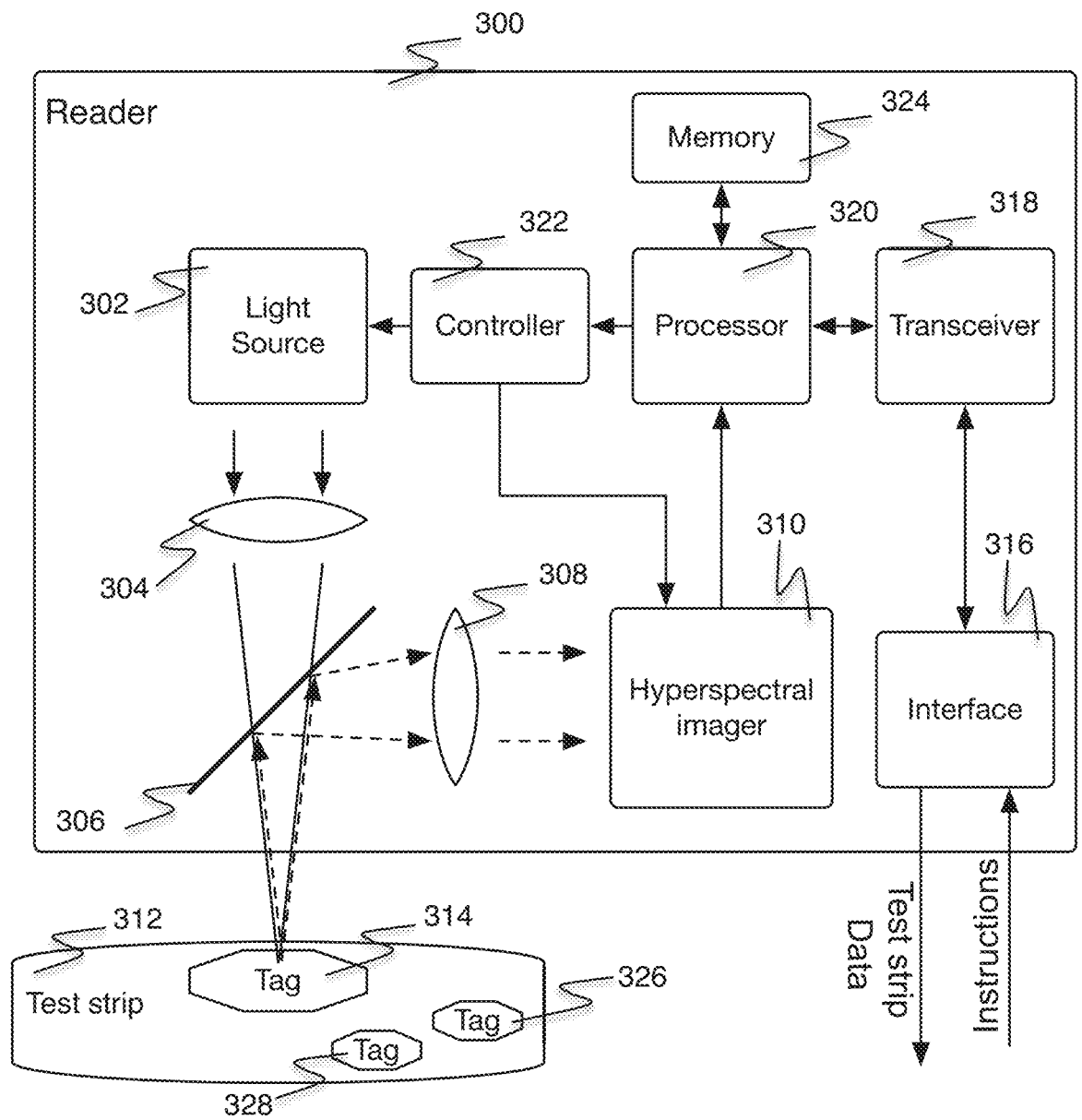
FIG. 3 is a block diagram illustrating an embodiment of a reader reading a test strip.

FIG. 3 is a block diagram illustrating an embodiment of a reader reading a test strip. In some embodiments, reader 300 is used to implement reader 200 of FIG. 2 or reader 100 of FIG. 1. In the example shown, reader 300 comprises light source 302, source lens 304, beam splitter 306, detector lens 308, hyperspectral imager 310, interface 316, transceiver 318, processor 320, controller 322, and memory 324. Test strip 312 comprises optical tags (e.g. tags 314, tags 326, tags 328) in a correct position for measurement by hyperspectral imager 310. In some embodiments, test strip 312 comprises one or more optical identification tags. In the example shown, light is emitted from light source 302 and focused by source lens 304 onto test strip 312. On the way to test strip 312, light passes through beam splitter 306. The light is then reflected from test strip 312 through beam splitter 306 and is collimated by detector lens 308. Light is collected and analyzed by hyperspectral imager 310. In the example shown, detector lens 308 sits in the image plane of the reflected light. In some embodiments, detector lens 308 is not present and hyperspectral imager 310 sits in the image plane of the reflected light. Processor 320 receives information about test strip 312 from hyperspectral imager 310 and sends it to transceiver 318 for output via interface 316. In some embodiments, processor 320 receives information about test strip 312 from hyperspectral imager 310 and stores it in memory 324. Reader 300 receives instructions for reading via interface 316. Interface 316 sends instructions to processor for processing via transceiver 318. Processor 320 controls the hyperspectral imager 310 and the light source 302 via controller 322.

In some embodiments, a software program installed on reader 300 may compare one or more spectral signature(s) from optical tags in a reference image stored in memory 324. The program executed by processor 320 may then identify those optical tags that demonstrate a spectral shift greater than a pre-determined threshold. The threshold may be set to distinguish one or more spectral shifts from standard measurement noise and/or one or more spectral shifts resulting from a non-specific molecular interaction. The program then decodes the optical spectral code in the shifted spectra optical tags. In some embodiments, the software program is computer readable medium storing instructions in memory 324 that when executed by processor 320 within reader 300, cause the processor to perform certain actions such as instructing controller 322 to read the test strip, or change light source 302 characteristics, or store certain data in memory 324. In some embodiments, the software program comprises one or more software modules that perform each of the various functions described above for the reader.

Compositions comprising a plurality of optical tags may be flowed across a surface or through a fluidic channel of a substrate. Upon contact, the plurality of optical tags may be allowed to contact or settle onto the substrate via gravity. Alternatively, upon contact, the plurality of optical tags may be guided into contacting the substrate via a direct or alternating electric, magnetic or electromagnetic field.

In some embodiments, the substrate or an optical tag may contact a solution containing the sample to be interrogated. In some embodiments, the substrate or an optical tag may be exposed to a gaseous or vapor phase comprising the sample to be interrogated.

In some embodiments, functionalized optical tags or substrates comprising functionalized optical tags are heated or cooled relative to ambient or room temperature to facilitate binding or other interactions of a target entity with a reactive moiety of a probe. In some embodiments, functionalized optical tags or substrates comprising functionalized optical tags are physically or mechanically disturbed (e.g., by vibration) to facilitate binding or other interactions of a target entity with a reactive moiety of a probe.

In some embodiments, a sample is applied to a substrate comprising a plurality of functionalized optical tags on the surface of the substrate, and any unbound material is subsequently washed away. In some embodiments, a substrate with aptamer-functionalized tags is incubated with a target protein solution (in phosphate buffered saline with Tween® (PBS-T)) for 1 hour. After removal of the protein solution and washing the substrate with PBS, the sample may be incubated for 30 min in phosphate buffered saline (PBS) before detection of a spectral signature from each of the optical tags to determine binding of the target protein to the aptamer bound to the optical tag.

In some embodiments, a plurality of unique functionalized optical tags are incubated with the target in solution and then filtered through a filter with pores smaller than the size of a majority of the tags. The filter is then dried and optical tags on the filter are imaged and analyzed using a hyperspectral reader as described herein.

In some embodiments, the functionalized optical tags can be exposed to a sample in vapor or gas form, then applied to a substrate for detection of a spectral signature to indicate whether a target molecule was present in the vapor or gas.

Figure 4A:
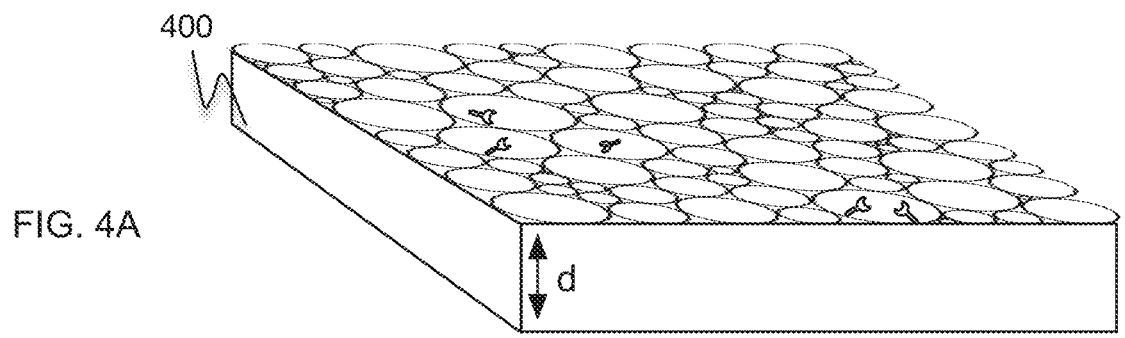
FIGS. 4A, 4B, and 4C are diagrams of a portion of a functionalized optical tag.
Figure 4B:
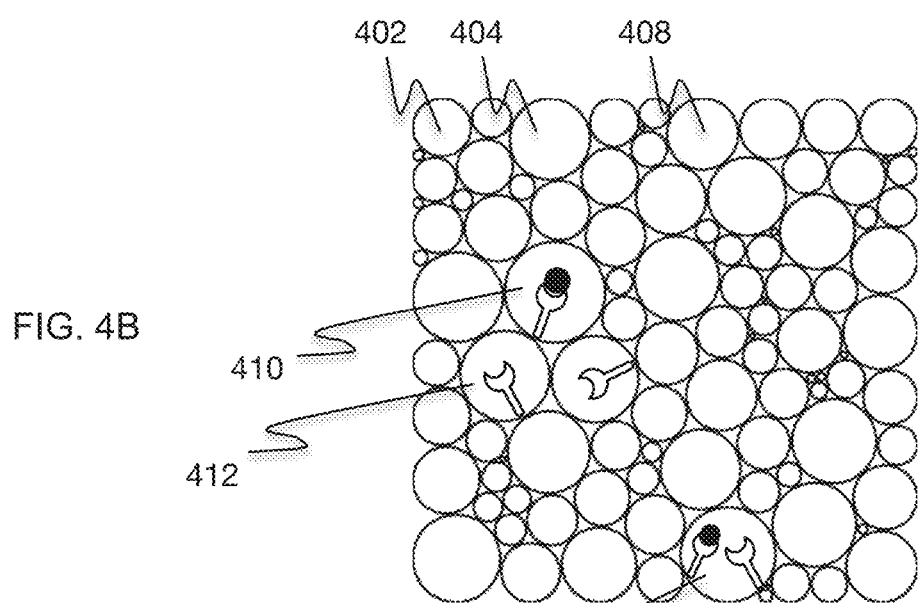
Figure 4C:
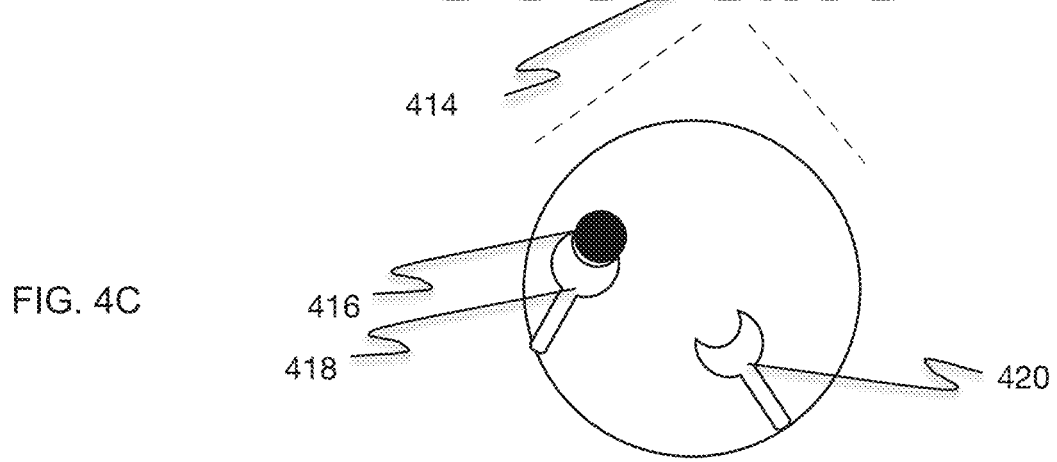

FIGS. 4A, 4B, and 4C are diagrams of a portion of a functionalized optical tag. A functionalized optical tag comprises a probe bound to the surface or pore of the optical tag, wherein the probe is capable of binding to a target of interest. In the example shown, porous optical tags can comprise silica, a non-silica, a pure or partially pure dielectric, or a partially oxidized silicon. In some embodiments, the porous optical tags further comprise a reactive moiety (e.g., probe) capable of binding at least one target entity. FIG. 4A is a perspective drawing of a portion of a functionalized optical tag 400 to show the thickness d of the optical tag 400. FIG. 4B is a plan view of the functionalized optical tag 400 in FIG. 4A. Optical tag 400 comprises pores (e.g., pore 402, pore 404, and pore 408) of a porous silicon film with a thickness d. Pore 410 shows an example of a probe bound to a target. Pore 412 shows an example of a probe unbound to a target. FIG. 4C shows a zoom of pore 414 of FIG. 4B. In FIG. 4C, probe 418 is bound to target 416 while probe 420 is unbound to a target.

Optical tags are functionalized by binding a probe capable of reacting with at least one target molecule. Each unique optical tag (i.e., each tag with a unique pore structure or optical thickness d) gives rise to a unique optical signature upon exposure to electromagnetic radiation. This unique optical signature is correlated with at least one probe comprising the reactive moiety bound to the pore. Thus, the substrate can be used for multiplexed detection wherein at least two unique optical tags in the plurality comprise a different reactive moiety each capable of reacting with a respective unique target molecule. The unique optical signature generated by each unique optical tag when exposed to a source of illumination can then be used to determine the identity of the reactive moiety and or target molecule that reacts with the reactive moiety.

Provided herein are functionalized optical tags that comprise a probe bound to the surface of the optical tag, wherein the probe is capable of binding to a target of interest. The optical tag acts as an identifier of the probes bound to its surface by having a series of structures that generate a unique, readable spectral response that is observed by analyzing reflected or transmitted light either from, or through, these optical tags, respectively called "reflectance spectra" and "transmission spectra".

Compositions of the disclosure have several design features that provide superior properties. Porous silica optical tags can be organically functionalized—for example, with silane-based compounds. Moreover, the large surface area of the optical tags increases the probability of a binding reaction to a target molecule and increases the sensitivity of the detection of the target molecule. Using a light source of multiple wavelengths, spectroscopic analysis can reveal spectral features in the reflected or transmitted light, such as the wavelength, amplitude, phase, and/or number of spectral peaks or troughs. These spectral features contain encoded information useful to determine the identity of an optical tag. The encoded information can be used to identify which probes are bound to the optical tag, or for determining the identity of a target molecule that binds to or otherwise interacts with the optical tag.

Porous silicon films have been shown to exhibit spectral properties dependent on thickness, porosity, and pore diameter. The pores are produced by means of an electrochemical etching wherein the etching current density determines the porosity, which is the volumetric fraction of the pores inside a layer of film, and the modulated structure of each pore in the film. The film's porosity relates directly to the material's effective optical index of refraction. More porosity leads to a lower refractive index because the dielectric effective medium contains more air.

As a general overview, the optical tags can be encoded with unique signatures that can serve as a unique optical spectrum code for each tag or a component of the unique tag code, which are analogous to barcodes or digital fingerprints used to reference objects in a database. The unique signatures are associated with how each optical tag is configured to interact with electromagnetic waves. The optical tags can be scanned with an emitter of an electromagnetic wave or other source of electromagnetic waves. A receiver receives an energy spectrum (i.e., a "spectral response" or a "reflectance or transmission spectrum"), which is based on the interaction of the optical tag with the electromagnetic wave. In some instances, the emitter and receiver may be a single device collectively referred to as a "tag reader."

The energy spectrum will have distinguishable spectral features. The characteristics of these one or more spectral features may be used to determine the unique spectral signature associated with the optical tag using various methods. Examples of the spectral features include spectral peak positions, spectral peak amplitudes, side lobes, and any other identifiable feature in the energy spectrum. Generally, these spectral features of the received spectral signature will be related to various configurable inputs used in manufacturing the optical tag. The combination of those spectral features may be used to determine the unique spectral signature associated with an optical tag, which may then be used to determine a unique optical spectrum associated with the object.

Porous silica or silicon optical tags (i.e., "microtaggants" or "tags" or "particles") can be used for the detection of biological and chemical analytes. Silica can be organically functionalized—for example with silane-based compounds. The large surface area of the optical tags increases the probability of a binding reaction, and therefore increases sensitivity of the detection. In various embodiments, optical tags comprise one of the following materials: silicon, fully- or partially oxidized silicon, silicon nitride, doped silicon, or any other appropriate material. Partially oxidized tags have a refractive index which is significantly higher than that of pure silica, which can facilitate an improved signal comprising a spectral signature. In some embodiments, optical tags comprise silica that is considered generally recognized as safe (GRAS) for their intended use in compliance with the Federal Food, Drug, and Cosmetic Act and its implementing regulations.

If a silicon or silica porous thin film or fragment thereof with parallel top and bottom surfaces (e.g., an optical tag) is illuminated with light, certain wavelengths will be reflected preferentially. Fabry-Perot fringes result from the interaction of light with the abrupt interfaces at the top and bottom surfaces.

Although provided herein as an example, optical tags are not limited to silicon-based materials. In some embodiments, an optical tag may be made from any porous material comprising pores that are both smaller than the wavelength of light and capable of generating a coded spectral response from an optical spectral code encoded in the optical tag. In some embodiments, an optical tag may be made from any porous material capable of generating a coded spectral response based on the index varying properties of the pores.

In some embodiments, the spectral signature of an optical tag is measured via a spectrum-resolving reader to generate a reference spectral signature. In some embodiments, the reference spectral signature is verified against other information as part of a database, such as reference spectral signatures of other tags. In some embodiments, a set of reference spectral signatures observed from optical tags from the same layer or wafer or multiple layers or wafers can be analyzed to assess a statistical distribution of reference spectral signatures for the modulated pore parameters in the optical tag.

The optical tags are passive, inconspicuous and can be attached to the various substrates such as paper, plastic and glass. In some embodiments, a collection of optically-encoded silica tags is provided, each comprising a modulated porous structure encoded by the same or similar signal, thus generating a substantially similar spectral signature upon illumination—these can collectively be referred to as being a first type of silica tags or silica tags of a first type.

Although embodiments of silica-based optical tags are taught, the optical tags can be generated using any material suitable to generate a spectral signature comprising a spectral response of an index varying filter. This can include any non-silica dielectric material with a refractive index sufficiently different from air to enable accurate detection and identification of a unique spectral signature.

In some embodiments, the optical tags are functionalized to facilitate binding of a probe to the optical tag. Preferably, functionalization occurs after the desired oxidation, if any is performed. In some embodiments, a linker, such as a silane linker, is bound to the optical tag. In some embodiments, the optical tag is bound to a linker at any point during the generation of the optical tag. For example, a silica wafer may be bound to a linker before the porous silicon thin film is removed from the wafer. A porous silica film removed from the wafer can be bound to a linker before it is sonicated to form individual optical tags. In some embodiments, a probe can be attached to the linker on a wafer prior to lift-off and sonication, or prior to sonication. A probe can also be attached to a linker of several individual optical tags from the same wafer (i.e., having a substantially similar modulated porous structure) after sonication.

In some embodiments, the optical tags comprising silica are functionalized with a thin layer of a linker, such as a silane, coated on the optical tags. Then, a specific probe is bound to the linker, thus functionalizing the optical tag with the probe.

In some embodiments, attachment of a target-specific probe to a functionalized optical tag comprises incubating a set of target-specific probe molecules with a solution comprising functionalized optical tags to allow binding of the target-specific probe molecules to the functionalized optical tags.

In some embodiments, the probe is an aptamer and is bound to a functionalized tag as follows: A 52 mM EDC solution (1-ethyl-3-(3-dimethylaminopropyl) carbodiimide) hydrochloride solution) is injected to a chamber containing the functionalized optical tags and allowed to react for 1 hour. Subsequently, 50 µL of 75 µM aptamer solution is applied to the optical tags for 1 hour, followed by thorough washing with 10 mL of 50 mM Tris buffer. This can be done through a filter with pores smaller than the optical tags. Finally, the aptamer is folded by incubation in PBS for 30 min.

In some embodiments, the probes are specific antigens. In some embodiments, the probes are enzymes. In some embodiments, the probes are antigen-associated antibodies. In some embodiments, the probes are oligonucleotides. In some embodiments, the probes are Peptide Nucleic Acids. In some embodiments, the probes are any molecule or optical tag with specific preferential bonding to a target analyte.

Probes comprising reactive moieties can be bound to the surface of a functionalized optical tag or within a pore of a functionalized optical tag, or a combination thereof. Thus, a reactive moiety can be present on the surface of an optical tag or in the pore of an optical tag, or both. In some embodiments, the reactive moiety is present only inside the pore of an optical tag (e.g., as part of a surface or volume within the pore).

Exemplary reactive moieties of the disclosure include, but are not limited to, at least a portion of a probe, such as a nucleic acid, an antibody, an aptamer, an antigen, an enzyme, a peptide nucleic acid, or any combination thereof. Exemplary target molecules of the disclosure include, but are not limited to, a nucleic acid, a protein, a carbohydrate, antibody, antigen, an inorganic molecule, an insecticide, a virus, a bacteria, a toxin, a hormone, or any combination thereof.

In certain embodiments, the reactive moiety of a probe may interact with the target molecule with high specificity, such as a high affinity binding reaction. The reactive moiety and the target moiety may interact via a covalent bond, such as a polar or nonpolar covalent bond, or via a non-covalent bond, such as an ionic bond, a polar bond, a hydrogen bond, a Van der Waals interaction.

In some embodiments, these optical tags are organically linked—for example via silanization, such that they are sufficiently uniformly coated yet the pore structure is not completely filled by the linker coating.

Without limiting the generality of the linking process, many methods for functionalizing silica surface are known to those familiar in the art. One is described herein as an example. A 1 mL aliquot of 0.5% 3-aminopropyltriethoxysilane (Aldrich Chemicals, Inc.) in ethanol is added to approximately $10^5$ optical tags and shaken for 1 h. The optical tags are washed with ethanol three times and once with acetonitrile in a centrifuge filter (Nanosep, 0.2 µm, Pall). Next, acetonitrile (980 µL), N,N-diisopropylethylamine (20 µL, Aldrich Chemicals, Inc.), and cyanuric chloride (10 mg, Aldrich Chemicals, Inc.) are added to the optical tags and the mixture is allowed to react for 2 h with constant shaking. The optical tags are then washed with acetonitrile 4 times, suspended in ethanol, and transferred to a microcentrifuge tube. The optical tags are settled by centrifugation at 4000 RPM and the supernatant decanted to a volume of approximately 25 µL.

In some embodiments, optical tag functionalization may be achieved as follows. The optical tags are incubated with a solution of 42 mM (3-Aminopropyl)triethoxysilane (APTES) in toluene for 1 h. After the solution is removed—for example, via filtration of the optical tags, the optical tags are washed with toluene, ethanol, and acetone and dried under a nitrogen stream—for example, in a chamber. The APTES-modified optical tags are then immersed in a freshly prepared solution of 100 mg of succinic acid in 4.7 mL of dimethyl sulfoxide (DMSO) and 300 µL of 0.1 M NaHCO3, pH 9.4 for 30 min. After removal of the solution, e.g., by filtration of the optical tags, they are washed extensively with DMSO two times and with purified water.

Compositions and/or substrates of the disclosure may be heated or cooled relative to ambient or room temperature to facilitate contact and/or binding of a probe comprising a reactive moiety to the surface of an optical tag.

In some embodiments, one or more batches of optical tags with different spectral signatures (e.g., where each of the batches with the different spectral signatures are referred to as a type of optical tag so that tags of a first, second, third type of optical tags each have their own signatures) are functionalized with specific probes, such that one probe species is exclusively associated with one or more spectral signatures (codes).

In some embodiments, one or more batches of optical tags with different spectral signatures are functionalized with specific probes, such that there may be some overlap between probe species and optical tag spectral signatures. By overlapping spectral signatures associated with a probe, one is still able to recover the identity of the bound target.

In some embodiments, functionalized optical tags with bound probes from different batches are mixed in powder form—for example, when the tags are dry.

In some embodiments, functionalized tags with bound probes from different batches are mixed in a buffer solution.

Figure 5:
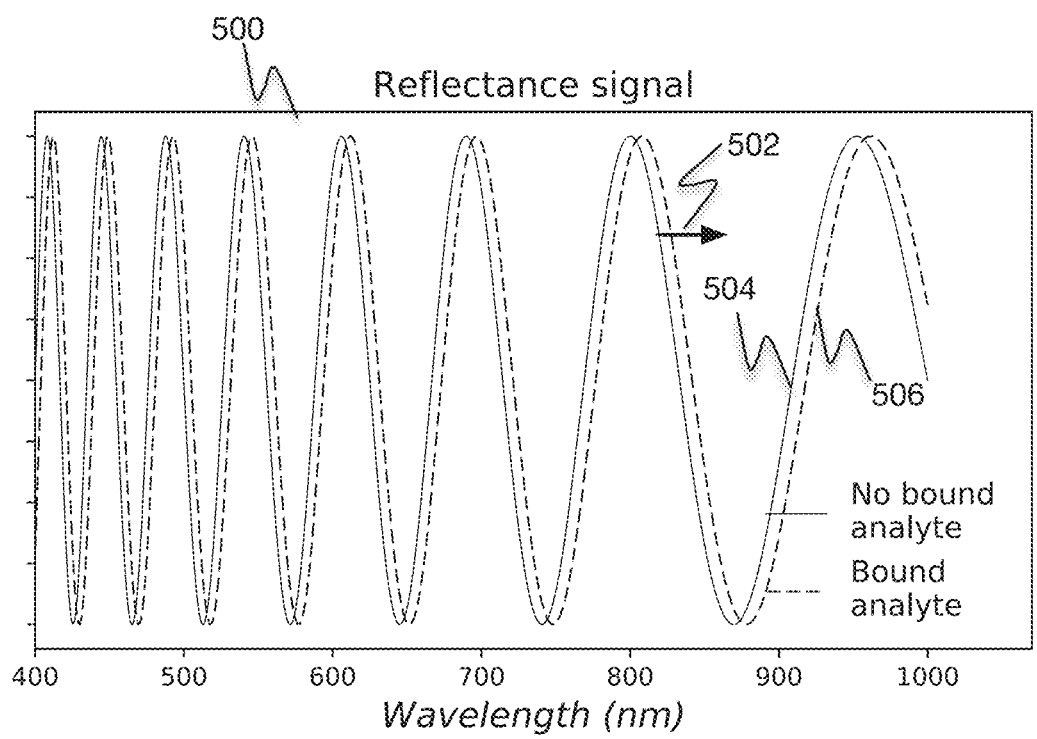
FIG. 5 is a graph illustrating an embodiment of a plot of the reflectance signal from a functionalized optical tag using a Fabry-Perot fringe model of a uniform 5 um thick porous film.

FIG. 5 is a graph illustrating an embodiment of a plot of the reflectance signal from a functionalized optical tag using a Fabry-Perot fringe model of a uniform 5 um thick porous film. In the example shown, while the intensity axis in plot 500 is normalized to one, the strength of the reflectance waveform will generally depend on the index of refraction change between the bulk of the tag film (e.g., porosity) and the material above and below the film layer (e.g., substrate). Waveform 504 is the expected reflectance signal from a 5 um thick uniform functionalized optical tag with no analyte bound. Waveform 506 is the expected reflectance signal from a 5 um thick uniform functionalized optical tag with analyte bound to the probe. The binding of the analyte to the probe causes shift 502 of the reflectance signal which can be detected by a reader such as 300 in FIG. 3. The thickness of the tag can be used to encode the probe type and can be determined by the reader using the fringe pattern of the reflectance signal (e.g., waveform 504).

In some embodiments, the unique identifier (i.e., spectral signature) of each optical tag can be read by a spectral reader. Readout of optical tag spectral signature can be done by detecting a reflected or transmitted spectral signal from the optical tags. This has traditionally been done using refractive optics, gratings or other spectrally dispersive mechanisms. These methods typically either analyze the spectrum from a spot or from a line. Therefore, in order to scan a region containing multiple porous silicon tags, the substrate can be scanned with respect to the light source and reflective probe, or vice versa. This typically results in an expensive system which includes moving stages, is less mechanical robust and therefore less amenable to being portable, is expensive, and requires a relatively long time to scan a large area with fine spatial resolution, which time is proportional to the ratio of total area to the required spatial resolution.

The development of tunable Fabry-Perot interferometers (FPI) in hyperspectral imaging is used by the methods of the disclosure to overcome many technical hurdles present when imaging distinct spectral signatures in a multiplexed reaction. FPI devices act as tunable filters with a wide spectral range and with fine spectral resolution. When placed in the illumination path between a white light source and a sample, a monochromator-type system may be constructed whereby one or a known number of narrow wavelength bands illuminate a target. When placed in the imaging arm of a system illuminating an object with white light, one or more wavelength bands of a transmitted optical signal and/or one or more wavelength reflection band(s) may be selected. When placed in the imaging arm of a system illuminating an object with white light, one or more of a known number of wavelength bands of a transmitted optical signal and/or one or more of a known number of narrow wavelength reflection band(s) may be selected. In some embodiments, the one or more wavelength reflection band(s) may be narrow wavelength reflection band(s). In the latter case, the FPI may either be placed in the Fourier plane of the imager or on the focal plane. The transmitted optical signal and/or reflected image may be detected by an area sensor. Thus, a relatively wide area can be scanned relatively quickly, with a wide spectral range and fine spectral resolution. For example, hyperspectral imaging devices and methods of the disclosure may provide a 100 $mm^2$ field of view, a 400 nm scan range with less than 10 nm resolution and a total acquisition time of less than 5 seconds. In various embodiments, the field of view comprises a field of view that is a few $mm^2$ to 1000 $mm^2$ or any other appropriate size.

Substrates of the disclosure may be imaged by a hyperspectral imager with sufficient spectral resolution to decode one or more spectral signatures from the optical tags as well as spectral changes caused by binding of a target molecule with a reactive moiety on the optical tags. Thus, in some embodiments, a single pixel of the image sensor on the hyperspectral imager may image, at most, a single optical tag.

Hyperspectral imagers of the disclosure may contain a tunable Fabry-Perot-Interferometer (FPI) whereby the FPI may be a component of either a monochromator-type instrument (i.e., the FPI selects narrow band(s) of illumination) or as a component of a spectrometer-type instrument (i.e., the FPI selects narrow band(s) of the transmitted optical signal and/or reflected signal to be imaged).

The spectra of all visible tags in the field of view may be concurrently collected via a reader with a tunable Fabry-Perot Interferometer (FPI). The location of individual optical tags may be determined by identifying unique characteristics of optical tag reflected signals versus reflected signals of the substrate (e.g., the existence of reflected spectral features). The location of individual optical tags may also be determined by identifying unique characteristics of optical tag transmitted optical signals versus transmitted optical signals of the substrate (e.g., the existence of transmitted optical spectral features).

In some embodiments, a high numerical aperture of the illuminating light may be accomplished by using, for example, a large diameter lens or a diffuser and a low numerical aperture of the imaging optics may be accomplished using—for example, a pupil, such that a plurality of optical tags having various spatial orientations can be illuminated but only the specular reflections are collected/measured.

In some embodiments, an illumination numerical aperture may be low, such that, for example, mostly collimated light illuminates the substrate, and a collection optics numerical aperture may be high, for example by using a large-diameter lens, such that specular reflections may be collected with high efficiency.

While a reflected signal shows spectral features, a transmitted optical signal would show the inverse of the reflected spectral features. When reading signals from optical tags of the disclosure, the transmitted optical signals may appear to be the inverse of the reflected signal.

In some embodiments, imaging a substrate comprising immobilized optical tags may include identifying a spectral change associated with at least one spectral feature (i.e., a "spectral shift"). In some embodiments, imaging a substrate comprising immobilized optical tags may include one of static imaging, stepper imaging, or scanning.

A reference hyperspectral image of a composition comprising a substrate and a plurality of optical tags may be recorded before the optical tags of the composition contact or bind a target molecule. The relative or absolute locations and select spectral features of the optical tags comprising reactive moieties bound to target molecules may be measured and recorded. To determine the presence of a spectral shift, a second sample hyperspectral image of the composition comprising a substrate and a plurality of optical tags may be captured after contacting a sample suspected of comprising a target entity. Here, a spectral shift would indicate a binding of a target entity to a reactive moiety bound to an optical tag. In some embodiments, a hyperspectral image of an optical tag is captured after a subsequent wash step.

Spectral shifts of the disclosure may include, by way of a non-limiting example, Fabry-Perot fringes. Fabry-Perot fringes result from reflected light between two planes of an optical tag. For example, in certain embodiments, optical tags of the disclosure may comprise at least two flat surfaces that are parallel to one another and reflections between these at least two flat surfaces may be Fabry-Perot fringes.

Figure 6:
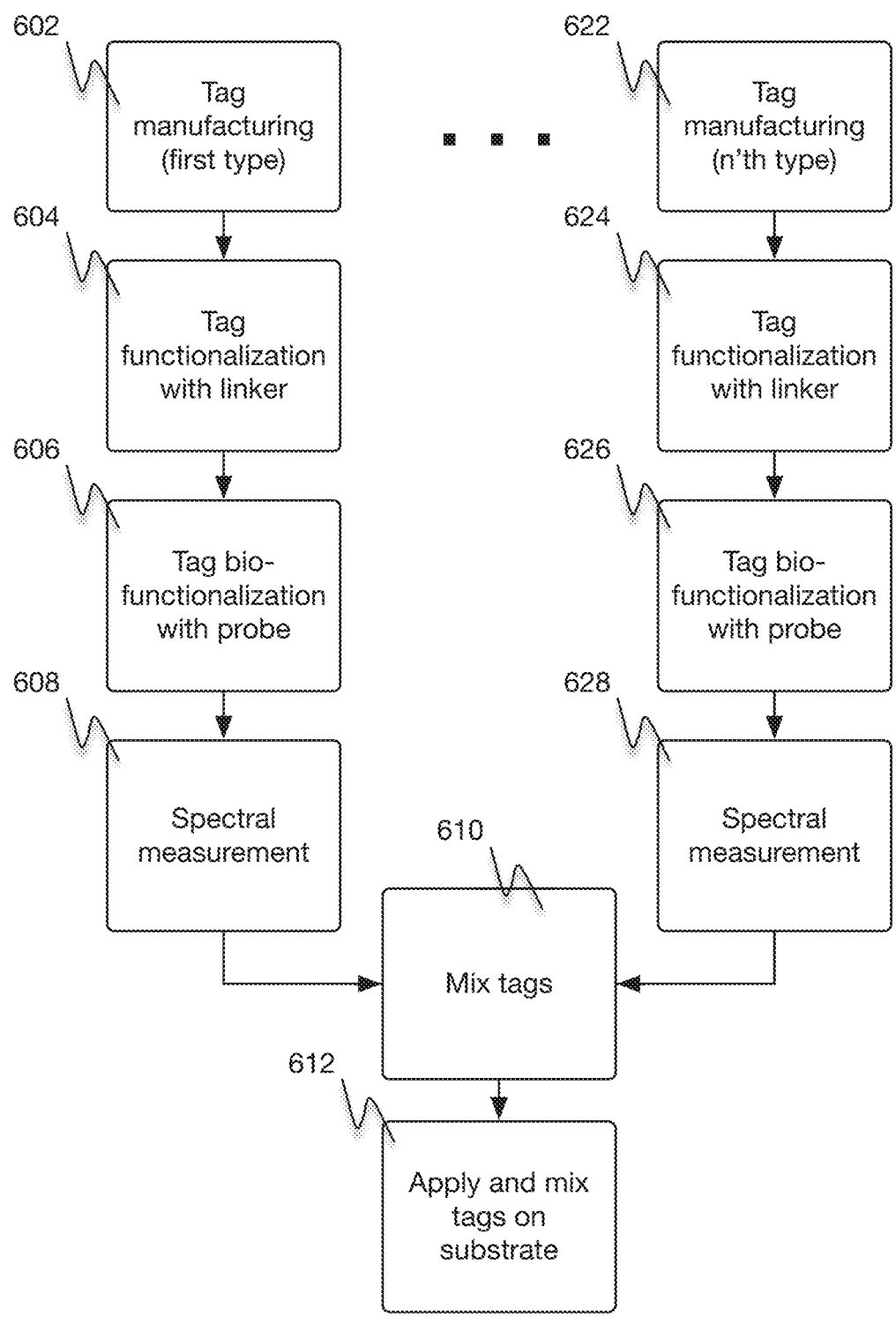
FIG. 6 is a flow diagram illustrating an embodiment of a method for a process of preparing a substrate.

FIG. 6 is a flow diagram illustrating an embodiment of a method for a process of preparing a substrate. In the example shown, the method is for generating unique functionalized optical tags and applying them to a substrate. It should be understood that the steps of the flow diagrams provided herein are illustrative only. In some embodiments, the illustrated steps are performed in different orders, certain steps are omitted, and/or additional steps not shown in the flow diagrams are performed. The method can start and end at various points in the process, and typically is a continuous process with multiple steps occurring simultaneously. So the flow diagrams, including FIG. 6, provide only an example of one ordering of method steps.

In the method of generating a substrate with a plurality of unique functionalized tags, the process includes generation of two or more unique functionalized optical tags each capable of generating a unique spectral signature each associated with one or more probes, reactive moieties, or target entities. A set of tags with a unique effective index of refraction and optical thickness of the optical tag are manufactured in 602, e.g., by etching a pore structure into a wafer, removing a layer comprising the wafer, and breaking the layer to form multiple optical tags. The set of unique optical tags is then functionalized with a linker in 604 and bound to a probe specific for a target analyte in 606. The probe is correlated with the unique optical thickness for the set of optical tags. A spectral measurement of one or more tags in the unique set of optical tags can be taken to determine a reference spectral signature in 608. The process of manufacturing in 602, functionalization in 604, probe binding in 606, and spectral signature measurement in 608 can be repeated n times for each of n sets of optical tags with unique optical spectral codes (e.g., in corresponding 622, 624, 626, and 628). The n sets of unique optical tags can then be added to a single mixture 610 and immobilized onto a substrate 612. Thus, a substrate capable of detecting multiple target analytes is generated, where the spectral signature from each optical tag can determine whether a target entity has reacted with a probe and the identity of the target entity from a plurality of possible target entities.

Substrates provided herein may comprise a plurality of optical tags immobilized to the surface, including, for example, at least 5, at least 10, at least 20, at least 50, at least 100, at least 500, at least 1,000, at least 10,000, or at least 100,000 optical tags. In some embodiments, the substrate comprises from 100 to 1,000 optical tags on the surface of the tag.

Compositions of the disclosure may include at least 10 unique optical tags immobilized to the surface of a substrate, each comprising a unique probe capable of reacting with a unique target entity from a set of at least 10 target entities, wherein the at least 10 optical tags each produce a unique spectral signature when illuminated. Compositions of the disclosure may include at least 50 unique optical tags immobilized to the surface of a substrate, each comprising a unique probe capable of reacting with a unique target entity from a set of at least 50 target entities, wherein the at least 50 optical tags each produce a unique spectral signature when illuminated. Compositions of the disclosure may include at least 100 unique optical tags immobilized to the surface of a substrate, each comprising a unique probe capable of reacting with a unique target entity from a set of at least 100 target entities, wherein the at least 100 optical tags each produce a unique spectral signature when illuminated. In some embodiments, the different reactive moiety and different spectral signature permit the identification of at least two different target molecules. In some embodiments, each optical tag having the same binding moiety or probe has the same spectral signature.

In some embodiments, multiple unique optical tags may be used to detect a single target, for example, whereby multiple probes specific to different regions of the targets may be incorporated on multiple respective tags, each containing a unique encoded spectral response.

The disclosure provides a method of obtaining a signal from a highly multiplexed, label-free assay, comprising contacting a substrate comprising a plurality of functionalized optical tags with a sample, the plurality of optical tags each bound to a probe with chemical or biochemical specificity for a target; incubating the sample to a predetermined percentage of completion of a reaction, such as a binding reaction or an enzymatic reaction; and imaging the substrate to obtain an output signal associated with at least one of the plurality of probes or targets. In some embodiments, the imaging comprises collecting a reflected signal or a transmitted signal. In some embodiments, a substrate comprising functionalized optical tags is lyophilized and or otherwise packaged dry to facilitate long term storage. The substrate can be can be reconstituted before use. In some embodiments, a substrate comprising functionalized optical tags is packaged in a buffer solution such that the functional probes are minimally degraded over time.

Figure 7:
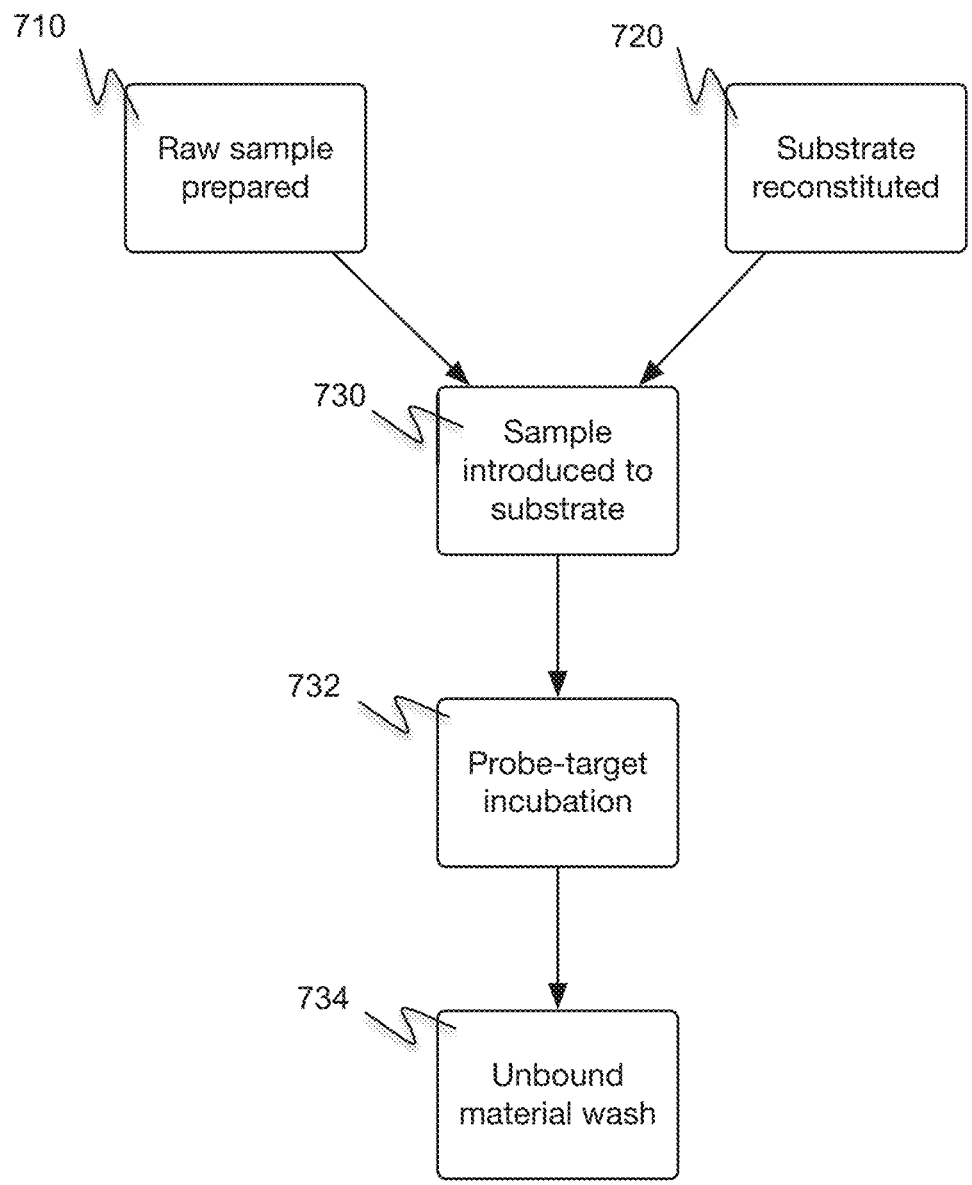
FIG. 7 is a flow diagram providing a method for an analyte binding to a substrate comprising optical tags.

FIG. 7 is a flow diagram providing a method for an analyte binding to a substrate comprising optical tags. A sample can be collected and optionally undergo selected reactions to increase the detection of analytes therein, including filtration, isolation, or amplification of analytes in 710. If the substrate has been used previously, it can be reconstituted in 720. When both substrate and sample are ready, the substrate contacts the sample in 730. Binding of an analyte to probes bound to optical tags on the substrate may be facilitated through incubation of the sample with the substrate in 732. Before detection, the substrate can then be washed to remove unbound or weakly bound molecules from the optical tags in 734.

In some embodiments, the imaging comprises identifying a spectral shift associated with at least one spectral reference feature in a spectral signature. In some embodiments, the imaging comprises one of static imaging, stepper imaging, or scanning. In some embodiments, before the receiving, the method comprises identifying an optical signal from the solid surface. In some embodiments, the method comprises comparing the optical signal identified from the solid surface with the output signal associated with the at least one probe. In some embodiments, the imaging comprises collecting a reflected signal or a transmitted signal. In some embodiments, imaging refers to collection of a hyperspectral image.

In some embodiments, the substrate is imaged by a hyperspectral imager with sufficient spectral resolution to decode the optical spectral codes from the tags as well as spectral shifts caused by binding of a target with a probe, such that in high likelihood, a single pixel of the image sensor on the hyperspectral imager will image at most a single tag. In some embodiments, the hyperspectral imager contains a tunable Fabry-Perot Interferometer (FPI) whereby the FPI is used to form either a monochromator-type instrument or to form a spectrometer-type instrument.

In some embodiments, the numerical aperture of the illuminating light is set to be high—for example, by using a large diameter lens or a diffuser, and the imaging numerical aperture of the imaging optics is low—for example by using a pupil, such that a large population of tags of various spatial orientations can be illuminated but only the specular reflections are collected. In some embodiments, the illumination numerical aperture is low, such that, for example, mostly collimated light illuminates the substrate, and the collection optics numerical aperture is high, for example by using a large-diameter lens, so that specular reflections may be collected with high efficiency.

In some embodiments, the spectra of all visible tags in the field of view is concurrently collected via a reader with a tunable FPI. In an embodiment, the location of individual tags is determined by identifying unique characteristics of tag reflected signals versus that of the substrate, such as the existence of reflected spectral peaks or troughs. In another embodiment, the tags are imaged with a non-FPI imager, which imager can resolve sufficient spatial and spectral features from the substrate containing the tags as to resolve individual tags and infer their optical spectral code.

In some embodiments, imaging a substrate comprising functionalized optical tags may include one of a direct or indirect reaction monitoring. For example, in the case of direct reaction monitoring, the position of certain spectral features of the optical tags on a substrate prior to the reaction taking place is either known or is measured. While the sample has been flowed onto the substrate and the target molecules react with the optical tags on the substrate, a spectral signal is recorded from the various optical tags. The difference between the signal from any optical tag during the incubation phase and the baseline signal from the same optical tag is a function of the refractive index shift versus baseline. This shift results from infiltration of the buffer solution into the pores, from diffusion of non-specific molecules into the pores, and from specific binding of target molecules onto the pore surface. The first two processes are static over time, resulting in a constant spectral shift with a Poisson noise. The last process is time-varying. By monitoring the reflectance spectrum in situ during the incubation we can use the different time scales of each process to separate their effects. This process can be detected either directly via the refractive index shift due to the incorporation of the target molecules or indirectly, for example if the incorporation of the target molecule on the surface of the pores induces a change in the hydrophobicity of the surface thus either forcing water out or letting water molecules into the pore and thus generating an amplified optical signal.

In some embodiments, a reference hyperspectral image of the tagged substrate is recorded before the introduction of the sample to the optical tag. In some embodiments, where the optical tag is immobilized on the surface of a substrate before contacting with a sample, a relative or absolute location and select spectral features of a reference spectral signature of each optical tag can be determined and saved. Features of the reference spectral signature from each optical tag can be compared with a spectral signature obtained from the optical tag after contacting the sample suspected of comprising a target molecule. This comparison can determine whether a spectral shift, indicative of the binding of a target molecule to a reactive moiety of a probe bound to the optical tag, is present. The reference spectral signature associated with at least one optical tag or optical tag bound to a reactive moiety, whether bound to a substrate or not, may be previously determined in a separate experiment or provided through—for example, a database.

In some embodiments, a hyperspectral image of an optical tag immobilized on the surface of a substrate is captured after contacting the sample suspected of comprising a target molecule, and, optionally after a wash step. A software program can be used to match spectral signatures from optical tags on the substrate with the reference spectral signatures for each optical tag, and to compare the spectral features of the reference and sample spectral signatures to determine whether there has been a spectral shift. The program can annotate those optical tags which display a spectral shift greater than a pre-determined threshold, which threshold is greater than standard measurement noise and the shifts resulting from non-specific molecular interaction. The program can also assess the shifts of many tags in aggregate, and based on the shift statistics gathered, report: (1) a likely concentration of the target analyte, and (2) an estimated probability associated with the result. The program can then decode the optical spectral code in the shifted spectra tags.

Target molecules may bind to more than one optical tag, each having a distinct reactive moiety, in a multiplex reaction. In some embodiments, a software program may be used to determine the identity of the target molecule when a spectral shift has been detected in a specified plurality of optical tags in the multiplex reaction.

Figure 8:
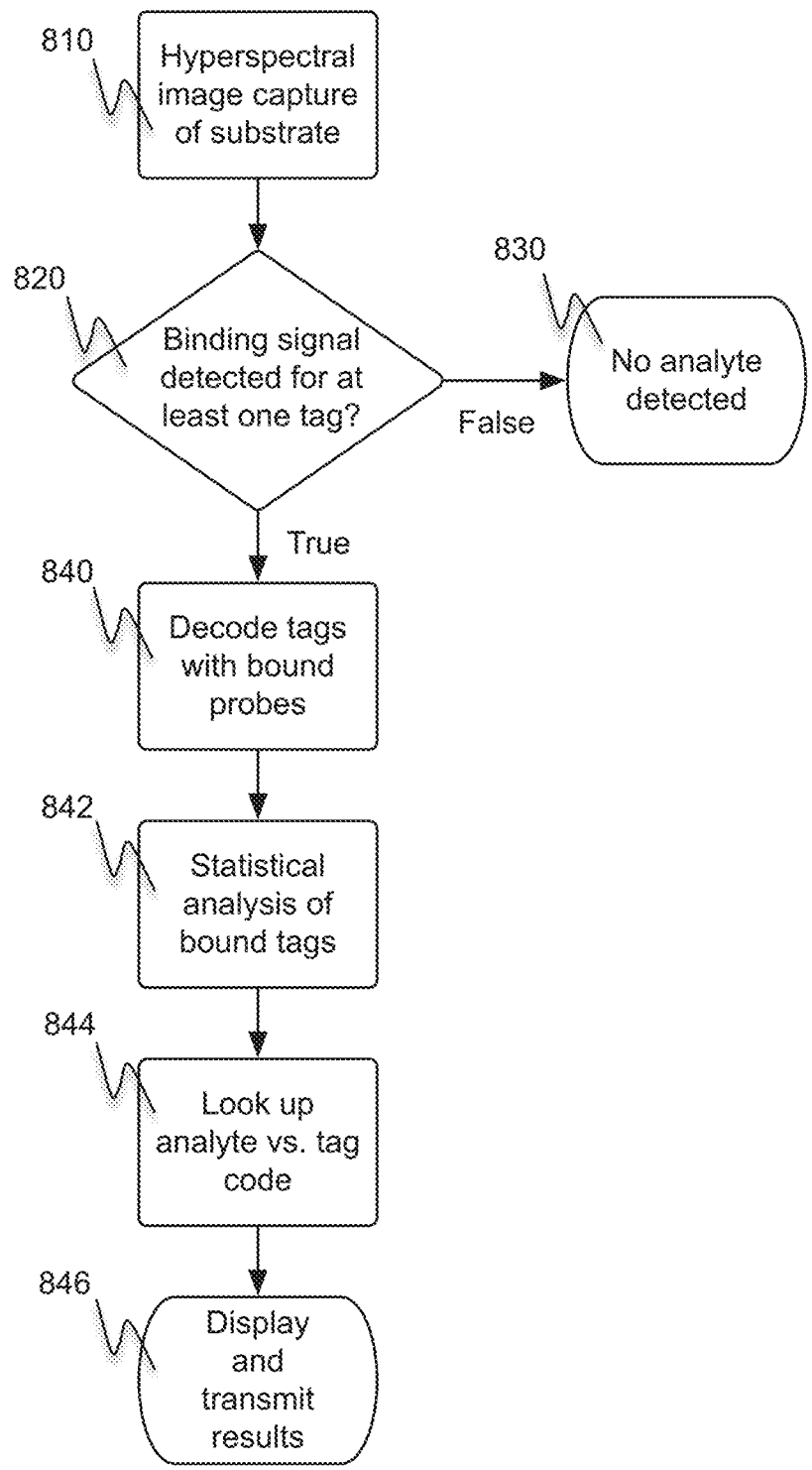
FIG. 8 is a flow diagram illustrating an embodiment of a process for providing a method for sample analysis flow using an observed spectral reference from the optical tag.

FIG. 8 is a flow diagram illustrating an embodiment of a process for providing a method for sample analysis flow using an observed spectral reference from the optical tag. In the example shown, a sample spectral signature of individual optical tags exposed to a sample is captured using an imager in 810. The sample spectral signature is used to determine whether or not there has been a binding interaction with a probe bound to the optical tag in 820. If no shift in spectral signature is detected, that indicates that no binding interaction occurred in 830. If a shift in spectral signature is detected in 840, a statistical analysis of the bound tags can be performed in 842, and the analyte identity determined by linking the spectral code to a unique spectral code of an optical tag in 844. The results can be displayed and/or transmitted to another entity in 846.

Figure 9:
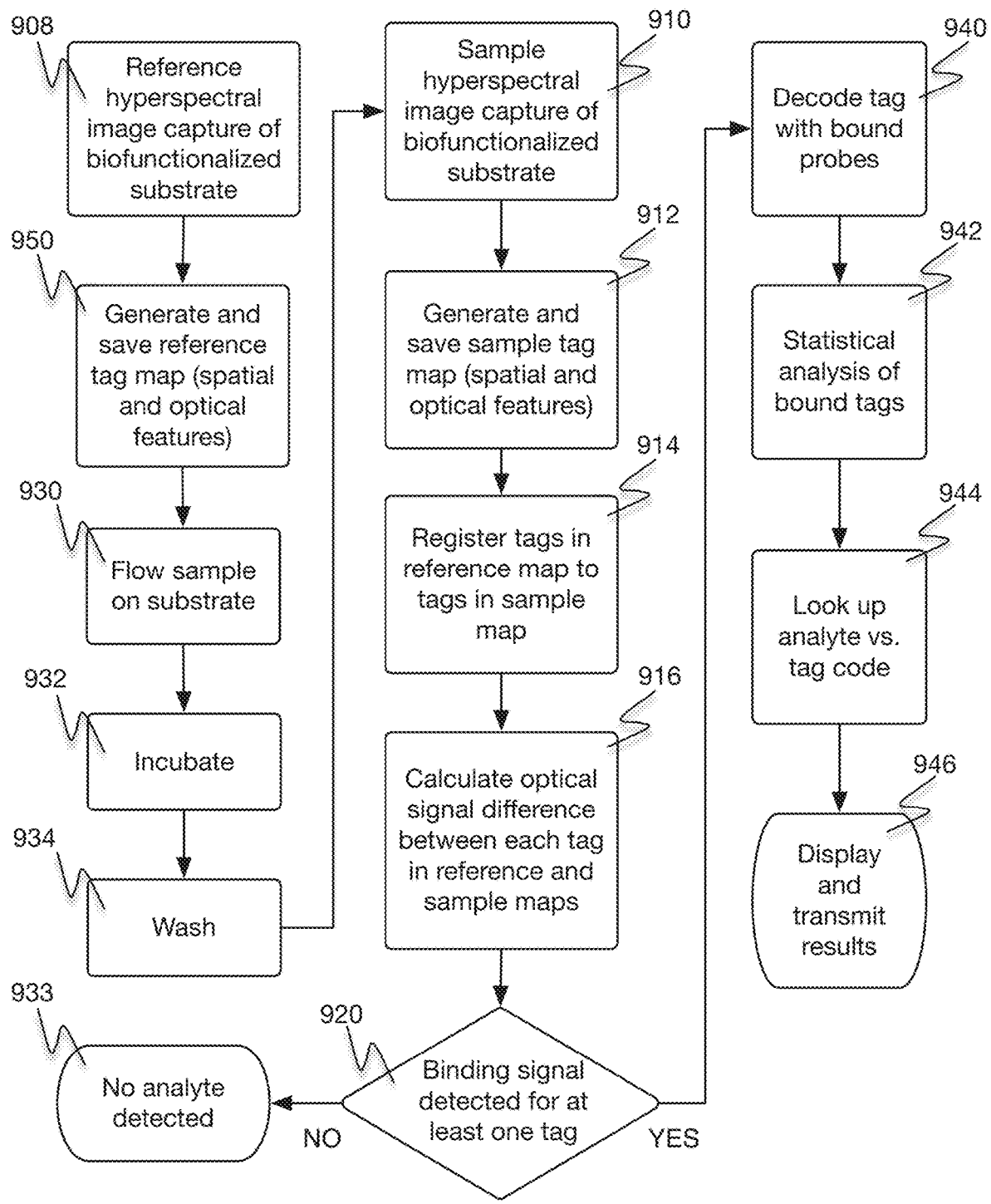
FIG. 9 is a flow diagram illustrating an embodiment of a process for providing a method for detecting a target analyte.

FIG. 9 is a flow diagram illustrating an embodiment of a process for providing a method for detecting a target analyte. In the example shown, detecting a target analyte is achieved by comparing a sample spectral signature with a reference hyperspectral signature taken before contacting the optical tag with the sample, and transmission of results. Here, a reference spectral signature is taken from each optical tag after functionalization and binding to the probe in 908. The reference spectral signature is processed to generate a reference tag map with—for example, spatial and optical features of the reference spectral signature, and saved to a memory in 950. A sample is prepared and flowed on the substrate in 930. Binding of an analyte to probes bound to optical tags on the substrate may be facilitated through incubation of the sample with the substrate in 932. Before detection, the substrate can then be washed to remove unbound or weakly bound molecules from the optical tags in 934. A sample spectral signature of individual optical tags exposed to a sample is captured using an imager in 910. The sample spectral signature is processed to generate a sample tag map with—for example, spatial and optical features of the sample spectral signature correlated with the reference spectral signature tag map in 912. The reference and sample tag map are compared in 914 to determine if there has been a shift in the spectral signature from an optical tag in 916. A determination is then made as to whether or not there has been a binding interaction with a probe bound to the optical tag in 920. If no shift in spectral signature is detected, that indicates that no binding interaction occurred in 933. If a shift in spectral signature is detected in 940, a statistical analysis of the bound tags can be performed in 942, and the analyte identity determined by linking the spectral code to a unique spectral code of an optical tag in 944. The results can be displayed and/or transmitted to another entity in 946.

In some embodiments, a known manufacturing specification is used as a reference for comparison to a sample spectrum signature. A sample hyperspectral image is collected as described herein and spectral features are compared with a known manufacturing specification of the functionalized tags. A software program annotates those tags which display a spectral shift greater than a pre-determined threshold versus the manufacturing specification, which threshold is greater than standard measurement noise and the shifts resulting from non-specific molecular interaction. The program then decodes the optical spectral code in the shifted spectra tags. In some embodiments, the identity of the target or targets corresponding to the shifted tags' optical spectral codes is looked up in a software lookup table.

A software program can be used to determine a binding of an analyte from the sample spectral signature based on a statistical analysis of the number of tags of each species which display a spectral shift. The statistical analysis can be based on a priori information regarding the sensitivity and specificity of each probe to its target in the presence of other analytes.

In some embodiments, a software program determines a binding of an analyte based on a statistical analysis of the number of optical tags having each reactive moiety that display a spectral change. This statistical analysis may be based on a priori information regarding the sensitivity and specificity of each reactive moiety to its target analyte in the presence of other pairs of reactive moieties and target molecules.

A multiplex reaction chamber comprising multiple optical tags with distinct reactive moieties may be incubated with one or more target. The substrate may be dried and imaged using a hyperspectral imager or any other sensing element able to detect and decode the encoded information as well as optical changes resulting from an incorporation of a target molecule. Spectral readers of the disclosure can resolve sufficient spatial and spectral features from a substrate comprising optical tags of the disclosure to resolve individual optical tags and identify their spectral signature(s).

A combination of the spectral shift measured in the optical tags and the number of optical tags in which the spectral shift is observed may be used along with binding sensitivity and optical tag number information to estimate the quantity of the target molecule detected.

Figure 10:
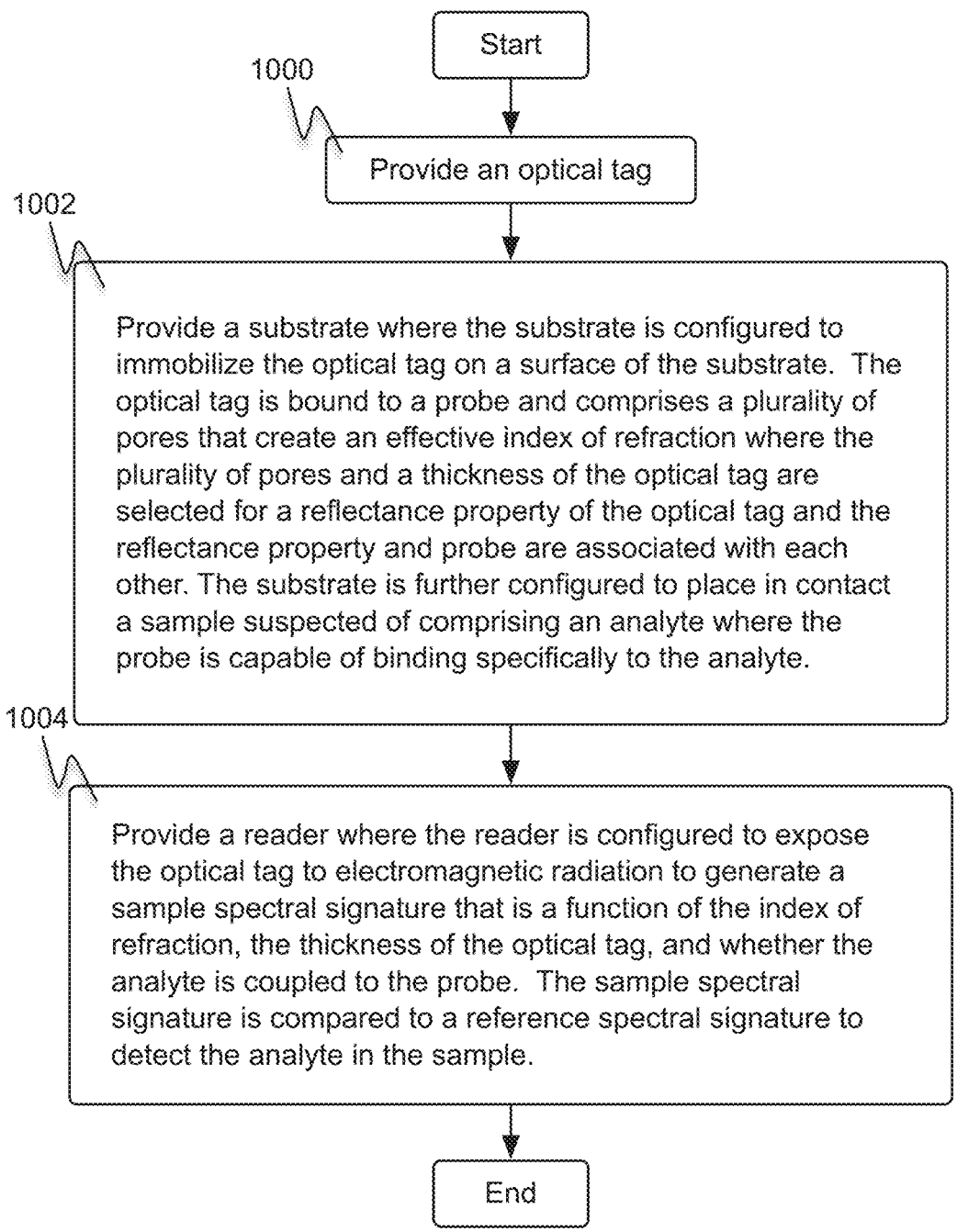
FIG. 10 is a flow diagram illustrating an embodiment of a process for a method of detecting an analyte suspected of being present in a sample.

FIG. 10 is a flow diagram illustrating an embodiment of a process for a method of detecting an analyte suspected of being present in a sample. In 1000, an optical tag is provided. In 1002, a substrate is provided where the substrate is configured to immobilize the optical tag on a surface of the substrate. The optical tag is bound to a probe and comprises a plurality of pores that create an effective index of refraction where the plurality of pores and a thickness of the optical tag are selected for a reflectance property of the optical tag and the reflectance property and probe are associated with each other. The substrate is further configured to place in contact a sample suspected of comprising an analyte where the probe is capable of binding specifically to the analyte. In 1004, a reader is provided where the reader is configured to expose the optical tag to electromagnetic radiation to generate a sample spectral signature that is a function of the effective index of refraction, the thickness of the optical tag, and whether the analyte is coupled to the probe. The sample spectral signature is compared to a reference spectral signature to detect the analyte in the sample.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system of detecting an analyte suspected of being present in a sample, comprising:
   a plurality of optical tags, wherein the plurality of optical tags are bound to a probe, wherein the plurality of optical tags comprise a plurality of pores that create an effective index of refraction, wherein the plurality of pores and a thickness of each optical tag are selected for a reflectance property of each optical tag, wherein the reflectance property and the probe are associated with each other, and wherein the thickness of each optical tag corresponds to a distance between a top of each optical tag and a bottom of each optical tag in plan view;
   a substrate comprising the plurality of optical tags immobilized on the surface of the substrate, wherein each of the plurality of optical tags is configured to generate a unique spectral signature comprising at least one peak that is a function of the effective index of refraction of an optical tag and the thickness of the plurality of optical tags, and wherein each of the plurality of optical tags includes a unique thickness different from other optical tags;
   a light source configured to:
      expose the plurality of optical tags on the substrate to electromagnetic radiation to generate a sample spectral signature, wherein the substrate is configured to immobilize the plurality of optical tags on a surface of the substrate, wherein the substrate is further configured to contact a sample suspected of comprising an analyte, wherein the probe is capable of binding specifically to the analyte, wherein the sample spectral signature is a function of the effective index of refraction, the thickness of each optical tag of the plurality of optical tags, wherein the sample spectral signature of each optical tag of the plurality of optical tags immobilized on the surface of the substrate taken after contacting the plurality of optical tags with the sample suspected of comprising the analyte, and whether the analyte is coupled to the probe, wherein the sample spectral signature is generated based on a first thickness of the each optical tag or a second thickness of each optical tag;

a hyperspectral imager coupled to the light source, the hyperspectral imager configured to generate the sample spectral signature;

a processor; and a non-transitory memory coupled with the processor, wherein the memory is configured to provide the processor with instructions which when executed cause the processor to:

read the plurality of optical tags on the substrate based on the sample spectral signature generated by the exposed plurality of optical tags, comprising to:

expose the plurality of optical tags to the electromagnetic radiation; and analyze, using the hyperspectral imager, electromagnetic radiation reflected by the plurality of optical tags to generate the sample spectral signature; and detect the analyte in the sample based at least in part on a comparison of the sample spectral signature of the plurality of optical tags with a reference spectral signature of the plurality of optical tags, wherein the reference spectral signature is based at least in part on a reference spectral image of the plurality of optical tags immobilized on the surface of the substrate taken before contacting the plurality of optical tags with the sample.

2. The system of claim 1, wherein the reference spectral signature is stored in the memory.

3. The system of claim 2, wherein the reference spectral signature is determined from a functionalized or non-functionalized optical tag before contact with said sample.

4. The system of claim 2, wherein the reference spectral signature is directly measured or statistically determined.

5. The system of claim 1, wherein the sample spectral signature comprises a Fabry-Perot spectral response.

6. The system of claim 1, wherein comparing the sample spectral signature with the reference spectral signature comprises identifying the presence or absence of a spectral signature shift between the sample spectral signature and the reference spectral signature.

7. The system of claim 6, wherein detection of the spectral signature shift indicates the presence of the analyte in said sample.

8. The system of claim 6, wherein the spectral signature shift comprises a shift in a peak placement or peak number.

9. The system of claim 1, wherein the plurality of optical tags comprise silica or silicon.

10. The system of claim 1, wherein the plurality of optical tags are partially oxidized or fully oxidized.

11. The system of claim 1, wherein the plurality of optical tags comprise a non-silica dielectric.

12. The system of claim 1, wherein the plurality of optical tags have a porosity of from 60 to 95%.

13. The system of claim 1, wherein the plurality of pores is sufficiently large to facilitate entry of the analyte into the plurality of pores while excluding non-target molecules.

14. The system of claim 1, wherein the plurality of optical tags comprise a silica linker.

15. The system of claim 14, wherein the linker is an organofunctional alkoxysilane molecule.

16. The system of claim 1, wherein the probe comprises an oligonucleotide or a polypeptide.

17. The system of claim 1, wherein the probe comprises a receptor, an aptamer, an antibody or an antibody fragment.

18. The system of claim 1, wherein the probe comprises a layer of amino acids across a surface of pores of the plurality of optical tags.

19. The system of claim 1, wherein the sample is a liquid, a gas, a vapor, or a solution.

20. The system of claim 1, wherein the substrate comprises glass, paper, plastic, a polymer, or any combination thereof.

21. The system of claim 1, wherein an identity of the probe is correlated with the unique optical tag.

22. The system of claim 1, wherein the hyperspectral imager comprises an interferometer.

23. The system of claim 22, wherein the interferometer is a tunable Fabry-Perot interferometer or a Michelson type interferometer.

24. The system of claim 1, wherein generating the sample spectral signature of the plurality of optical tags comprises obtaining a wide spectral range from a field of view of a few $mm^2$ to 1000 $mm^2$.

25. The system of claim 8, further comprising:

a display operatively coupled to the processor and configured to:

display an identity of the analyte upon detection.

26. The system of claim 1, wherein the analyte is label free.

27. The system of claim 1, wherein the probe is label free.

28. The system of claim 1, wherein each of the plurality of optical tags has a diameter, length, width, depth or height that is less than or equal to a millimeter.

29. The system of claim 1, wherein detecting the analyte in the sample comprises determining a presence or an absence of the analyte in the sample.

30. The system claim 1, wherein detecting the analyte in the sample comprises determining a property of the analyte in the sample.

31. The system of claim 30, wherein the property is a concentration of the analyte, a binding affinity of the analyte to the probe, or a specific activity of the analyte.

32. The system of claim 31, wherein the concentration is determined from a proportion of the plurality of optical tags generating a shifted spectral signature, or is determined from a change in an average spectral signature for the plurality of optical tags.

33. The system of claim 1, wherein the analyte undergoes a nucleic acid amplification reaction before contacting the plurality of optical tags with the sample, wherein the analyte is a polynucleotide.

34. The system of claim 33, wherein the nucleic acid amplification reaction is a polymerase chain reaction or an isothermal amplification reaction.

35. The system of claim 34, wherein the isothermal amplification reaction is a recombinase polymerase amplification reaction.

36. The system of claim 1, wherein the analyte is purified from the sample using magnetic beads.

37. The system of claim 1, wherein the sample is exposed to an electric field during contact with the plurality of optical tags.

38. The system of claim 1, wherein the substrate is washed to remove non-specifically bound molecules.

39. The system of claim 38, wherein said substrate is washed with buffer or air.

40. The system of claim 1, wherein contacting the plurality of optical tags with the sample comprises mixing the plurality of optical tags with the sample in a solution or in a gaseous environment.

41. The system of claim 1, wherein the plurality of optical tags are separated from the sample using centrifugation, filtration, or electrophoresis.

42. The system of claim 1, wherein the substrate comprises a filter with pores that are smaller than the size the plurality of optical tags.

43. The system of claim 1, wherein the sample spectral signature is determined based on a porosity of the plurality of optical tags, wherein the porosity of the plurality of optical tags is determined based on the plurality of pores, and wherein the porosity of the plurality of optical tags includes a first porosity of the plurality of optical tags or a second porosity of the plurality of optical tags.

\* \* \* \* \*